(12) United States Patent
Kimura et al.

(10) Patent No.: US 9,500,603 B2
(45) Date of Patent: Nov. 22, 2016

(54) MICROCRYSTAL STRUCTURE ANALYSIS DEVICE, MICROCRYSTAL STRUCTURE ANALYSIS METHOD, AND X-RAY SHIELD DEVICE

(71) Applicant: Kyoto University, Kyoto (JP)

(72) Inventors: Tsunehisa Kimura, Kyoto (JP); Fumiko Kimura, Kyoto (JP); Chiaki Tsuboi, Kyoto (JP)

(73) Assignee: Kyoto University, Kyoto (JP)

( * ) Notice: Subject to any disclaimer, the term of this patent is extended or adjusted under 35 U.S.C. 154(b) by 155 days.

(21) Appl. No.: 14/376,024

(22) PCT Filed: Feb. 6, 2013

(86) PCT No.: PCT/JP2013/052704
§ 371 (c)(1),
(2) Date: Jul. 31, 2014

(87) PCT Pub. No.: WO2013/118761
PCT Pub. Date: Aug. 15, 2013

(65) Prior Publication Data
US 2015/0010132 A1   Jan. 8, 2015

(30) Foreign Application Priority Data

Feb. 6, 2012  (JP) .................................. 2012-023212

(51) Int. Cl.
*G01N 23/00* (2006.01)
*G01N 23/207* (2006.01)
(Continued)

(52) U.S. Cl.
CPC ........ *G01N 23/207* (2013.01); *G01N 23/2005* (2013.01); *G21K 1/043* (2013.01); *G01N 2223/3306* (2013.01)

(58) Field of Classification Search
CPC ................... G01N 23/207; G01N 2223/3306; G01N 23/2005; G21K 1/043
See application file for complete search history.

(56) References Cited

U.S. PATENT DOCUMENTS 4,658,411 A * 4/1987 Argoud ................ G01N 23/207
                                                                        250/390.09

FOREIGN PATENT DOCUMENTS

JP          4-301800 A      1/2001
JP     2006-057055 A      1/2004
(Continued)

OTHER PUBLICATIONS

Matsumoto et al., Kenji; "X-ray Diffraction of a Magnetically Oriented Microcrystal Suspension of L-Alanine", Crystal Growth & Design. Division of Forest and Biomaterials Science, Kyoto University. Published Mar. 8, 2011.
(Continued)

*Primary Examiner* — David J Makiya
*Assistant Examiner* — Dani Fox
(74) *Attorney, Agent, or Firm* — Lewis Roca Rothgerber Christie LLP

(57) ABSTRACT

A microcrystal structure analysis apparatus includes: a magnetic field generation unit; a sample drive unit configured to rotate a sample container containing a sample having microcrystals suspended therein relative to the magnetic field generation unit such that a temporally varying magnetic field is applied to the sample container to three-dimensionally orient the microcrystals; an X-ray source configured to apply X rays to the sample container that is being rotated by the sample drive unit; an X-ray detection unit capable of detecting the X rays that have passed through and have been diffracted by the sample container; and a state switching device configured to cause a state where detection of the X rays by the X-ray detection unit is disenabled or a state where detection of the X rays by the X-ray detection unit is enabled, in accordance with a rotational position of a specific part which is a part of the sample container in a rotation direction thereof.

16 Claims, 16 Drawing Sheets

(51) Int. Cl.
*G01N 23/20* (2006.01)
*G21K 1/04* (2006.01)

(56) References Cited

FOREIGN PATENT DOCUMENTS

| JP | 2008-039699 | 2/2008 |
|---|---|---|
| WO | WO 2013/118761 | 8/2013 |

OTHER PUBLICATIONS

European Patent Application No. 13747037.3 Extended Search Report dated Sep. 30, 2015.
PCT Application No. PCT/JP2013/052704 International Preliminary Report on Patentability dated Aug. 6, 2014.
PCT Application No. PCT/JP2013/052704 International Search Report and Written Opinion mailed Apr. 16, 2013.
Kenji Matsumoto et al., "Anisotropic Magnetic Susceptibility of Biaxial Crystal Determined by X-ray Diffraction Measurement", The Magneto-Science Society of Japan Nenkai Program Yoshishu, Sep. 26, 2011, pp. 18 to 19.
Keiii Fujita et al., "Determination of Anisotropic Magnetic Susceptibility Ratio by X-ray Measurements", The Magneto-Science Society of Japan Nenkai Program Yoshishu, Sep. 26, 2011, pp. 114 to 115.
Tsunehisa Kimura, "kyoujiba wo mochiita bikesshou funmatsu no haikou seigyo -kaisetuhou, bunnkouhou eno ouyou—(Alignment of Powder Crystallites Under High Magnetic Field:Applications to Diffractometry and Spectroscopy)", Journal of the Japanese Society for Neutron Science, 2007, vol. 17, No. 1, 55 to 58 pages.
International Search Report for PCT/JP2013/052704 dated Aug. 15, 2013.

* cited by examiner

FIG. 9
(a)
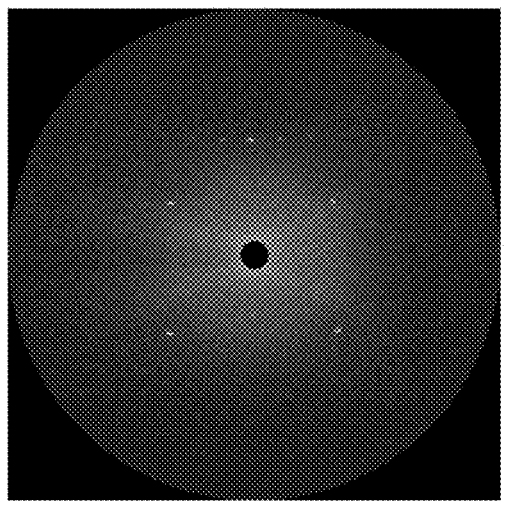
(b)
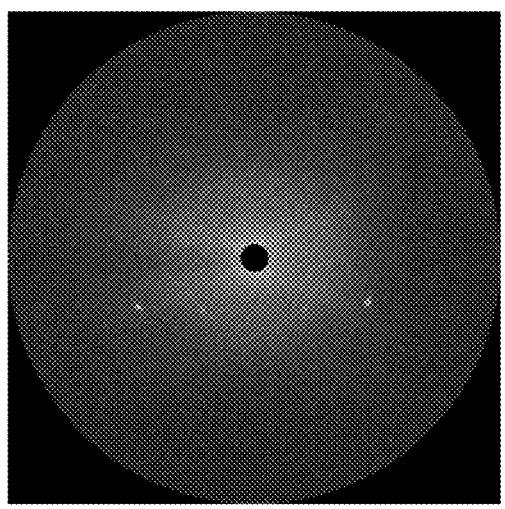

FIG. 13
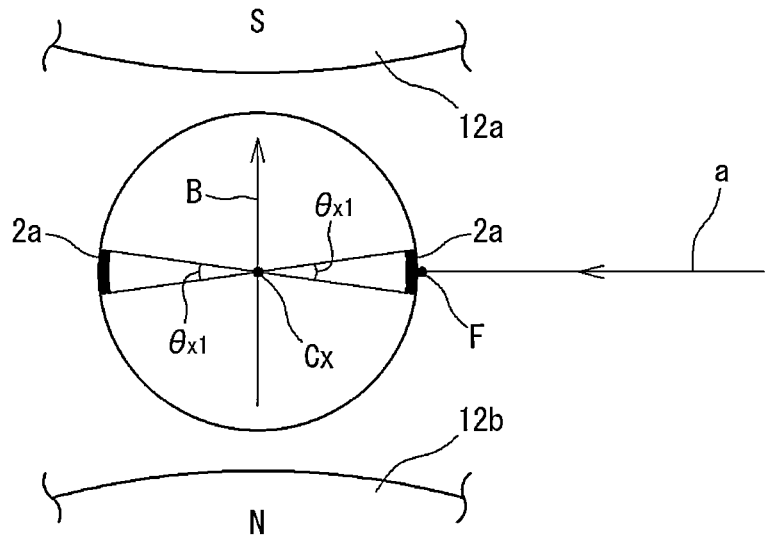
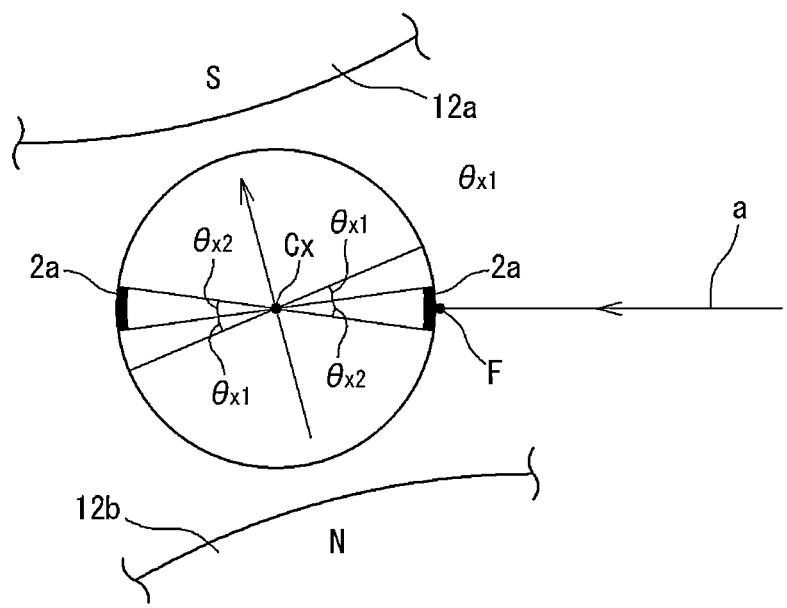

MICROCRYSTAL STRUCTURE ANALYSIS DEVICE, MICROCRYSTAL STRUCTURE ANALYSIS METHOD, AND X-RAY SHIELD DEVICE

CROSS-REFERENCE TO RELATED APPLICATIONS

The present application is a national phase application of PCT application PCT/JP2013/052704 filed Feb. 6, 2013, which claims the priority benefit of Japanese patent application 2012-023212 filed Feb. 6, 2012, the disclosures of which are incorporated herein by reference.

BACKGROUND

1. Technical Field

The present invention relates to a microcrystal structure analysis apparatus, a microcrystal structure analysis method, and an X-ray shielding device.

2. Background Art

X-ray structure analysis is known as analysis for the crystal structure of an object. The X-ray structure analysis is performed generally by using single crystals or microcrystal powder (hereinafter, referred to merely as "microcrystals") having a size of about 100 μm or greater. In recent years, a method has been developed in which microcrystals suspended in a sample are three-dimensionally oriented into a pseudo-single-crystallized state and analysis is performed in this state.

Regarding this method, conventionally, a method is known in which a temporally varying magnetic field is applied to a sample having microcrystals suspended therein to three-dimensionally orient (pseudo-single-crystallize) the microcrystals, then a suspending medium is cured with ultraviolet rays to fix the orientation of the microcrystals, and analysis is performed in this state (see, e.g., PATENT LITERATURE 1 and NON PATENT LITERATURE 1).

CITATION LIST

Patent Literature

PATENT LITERATURE 1: Japanese Laid-Open Patent Publication No. 2006-57055

Non Patent Literature

NON PATENT LITERATURE 1: Tsunehisa Kimura, "kyoujiba wo mochiita bikesshou funmatsu no haikou seigyo-kaisetuhou, bunnkouhou eno ouyou—(Alignment of Powder Crystallites Under High Magnetic Field: Applications to Diffractometry and Spectroscopy)", Journal of the Japanese Society for Neutron Science, 2007, VOL 17, No. 1, 55 to 58 pages

SUMMARY OF INVENTION

Technical Problem

In the conventional analysis method described above, since the suspending medium is cured, it is difficult to collect the microcrystals within the suspending medium after the analysis. In addition, the suspending medium contracts when being cured, and thus there is the problem that the orientation of the microcrystals is disturbed by the contraction.

Thus, the present applicant has proposed a method for performing X-ray structure analysis without curing a suspending medium (Japanese Patent Application No. 2011-033264; hereinafter, referred to as "prior invention"). In the prior invention, by rotating a sample having microcrystals suspended therein, a temporally varying magnetic field is applied to the sample to three-dimensionally orient the microcrystals to pseudo-single-crystallize the microcrystals, and then X rays are applied to the sample while the sample is rotated such that the orientation of the microcrystals is not disturbed, to perform structure analysis.

However, in the analysis method of the prior invention, since X rays are continuously applied to the pseudo-single-crystallized sample while the sample is rotated, it is not possible to apply X rays to the sample only when the sample is at a specific rotational position, and there is the problem that a favorable X-ray diffraction image cannot be obtained.

The present invention has been made in view of the above-described problems, and an object of the present invention is to provide a microcrystal structure analysis apparatus, a microcrystal structure analysis method, and an X-ray shielding device which allow a favorable X-ray diffraction image to be obtained even when X rays are applied to a pseudo-single-crystallized sample while the sample is rotated.

Solution to Problem

A microcrystal structure analysis apparatus of the present invention is a microcrystal structure analysis apparatus including: a magnetic field generation unit; a sample drive unit configured to rotate a sample having microcrystals suspended therein relative to the magnetic field generation unit such that a temporally varying magnetic field is applied to the sample to three-dimensionally orient the microcrystals; an X-ray source configured to apply X rays to the sample that is being rotated by the sample drive unit; an X-ray detection unit capable of detecting the X rays that have passed through and have been diffracted by the sample; and a state switching device configured to switch between a state where detection of the X rays by the X-ray detection unit is disenabled and a state where detection of the X rays by the X-ray detection unit is permitted, in accordance with a rotational position of a specific part which is a part of the sample in a rotation direction thereof.

In addition, a microcrystal structure analysis method of the present invention is a microcrystal structure analysis method including: rotating a sample having microcrystals suspended therein relative to a magnetic field generation unit, thereby applying a temporally varying magnetic field to the sample to three-dimensionally orient the microcrystals; applying X rays toward the sample while rotating the sample; detecting the X rays that have passed through and have been diffracted by the sample; and switching between a state where detection of the X rays is disenabled and a state where detection of the X rays is permitted, in accordance with a rotational position of a specific part which is a part of the sample in a rotation direction thereof.

According to the microcrystal structure analysis apparatus and the microcrystal structure analysis method of the present invention, the microcrystals are three-dimensionally oriented (pseudo-single-crystallized) by rotating the sample having the microcrystals suspended therein relative to the magnetic field generation unit. Then, the X rays are applied to the sample while the rotation of the sample is continued, and the X rays that have passed through and have been diffracted by the sample are detected, whereby it is possible to obtain an X-ray diffraction image of the pseudo-single crystals. At that time, it is possible to continue intermittent application of the X rays to the sample in a state where the specific part is directed in the desired direction, by switching between the state where detection of the X rays is disenabled and the state where detection of the X rays is permitted in accordance with the rotational position of the specific part. Thus, it is possible to obtain a favorable X-ray diffraction image even when the X rays are applied to the pseudo-single-crystallized sample while the sample is rotated.

The state switching device is preferably composed of an X-ray shielding device configured to shield application of the X rays when the specific part which is the part of the sample in the rotation direction thereof is not directed in a desired direction, and permit application of the X rays when the specific part is directed in the desired direction.

In this case, since application of the X rays is permitted only when the specific part of the sample is directed in the desired direction, it is possible to intermittently detect the X rays that have passed through and have been diffracted by the sample in a state where the specific part is directed in the desired direction, by the X-ray detection unit. Thus, it is possible to obtain a favorable X-ray diffraction image even when the X rays are applied to the pseudo-single-crystallized sample while the sample is rotated.

The X-ray shielding device preferably includes: a shielding portion switchable between a shielding position where the shielding portion shields application of the X rays and a permitting position where the shielding portion permits application of the X rays; a shielding drive unit configured to switch-drive the shielding portion; and a shielding control unit configured to control switch-driving of the shielding drive unit such that the shielding portion is located at the shielding position when the specific part is not directed in the desired direction; and the shielding portion is located at the permitting position when the specific part is directed in the desired direction.

In this case, since the shielding portion is switched from the shielding position to the permitting position only when the specific part of the sample is directed in the desired direction, it is possible to intermittently detect the X rays that have passed through and have been diffracted by the sample in a state where the specific part is directed in the desired direction, by the X-ray detection unit. Thus, it is possible to obtain a favorable X-ray diffraction image even when the X rays are applied to the pseudo-single-crystallized sample while the sample is rotated.

Preferably, the shielding portion includes a shielding portion main body formed in a disc shape and configured to shield application of the X rays at one surface thereof; and a slit formed in the shielding portion main body and configured to permit application of the X rays by causing the X rays to pass therethrough, the shielding drive unit is capable of rotary-driving the shielding portion main body about an axis thereof, and the shielding control unit controls driving of the shielding drive unit such that rotation of the shielding portion main body is synchronized with rotation of the sample.

In this case, if, before the shielding portion main body is rotary-driven by the shielding drive unit, a rotation start position of the shielding portion main body is previously set such that only when the specific part of the sample is directed in the desired direction, the slit of the shielding portion is located at a rotational position where the X rays are caused to pass therethrough, it is possible to apply the X rays only when the specific part is directed in the desired direction, by rotating the disc-shaped shielding portion main body in synchronization with rotation of the sample. Therefore, it is possible to intermittently detect the X rays that have passed through and have been diffracted by the sample in a state where the specific part is directed in the desired direction, and thus it is possible to obtain a favorable X-ray diffraction image with a simple configuration.

The slit is preferably formed at two locations in a circumferential direction on the shielding portion main body with an angle difference of substantially 180 degrees therebetween.

In this case, since it is possible to apply the X rays to the sample twice by causing the X rays to pass through the respective two slits while the shielding portion main body makes one rotation, it is possible to increase the application time per one rotation of the shielding portion main body as compared to the case where the slit is formed at only one location. Therefore, when an X-ray diffraction image obtained by applying the X rays in a state before the sample is rotated by 180 degrees and an X-ray diffraction image obtained by applying the X rays in a state after the sample is rotated by 180 degrees are the same, it is possible to obtain a favorable X-ray diffraction image in a short time.

The shielding portion is preferably arranged between the X-ray source and the sample.

In this case, since the shielding portion shields and permits application of the X rays that have not been scattered, it is possible to reduce the size of the shielding portion as compared to the case where the shielding portion is arranged between the sample and the X-ray detection unit, namely, the case where the shielding portion is arranged so as to shield and permit application of the X rays that have been scattered.

The shielding portion is preferably switchable between the shielding position and the permitting position by moving in a direction intersecting an application direction in which the X rays are applied. In this case, it is possible to obtain a favorable X-ray diffraction image with a simple configuration.

The shielding control unit is preferably capable of adjusting a timing at which the shielding portion is switched to each of the shielding position and the permitting position.

In this case, by adjusting the timing at which the shielding portion is switched to each of the shielding position and the permitting position, it is possible to change the position of the specific part of the sample to an arbitrary position along the rotation direction of the sample. Thus, it is possible to easily reset the specific part.

The shielding control unit is preferably capable of adjusting a time period for which the shielding portion is held at the permitting position.

In this case, by adjusting the time period for which the shielding portion is held at the permitting position, it is possible to change the size of the specific part of the sample to an arbitrary size. Thus, it is possible to easily change the size of the specific part in accordance with the type of the sample.

The shielding portion is preferably arranged between the sample and the X-ray detection unit.

Preferably, the X-ray source includes an X-ray window portion for emitting the generated X rays toward the sample; and a shutter configured to open and close the X-ray window portion, and the shutter is configured as the shielding portion.

In this case, since it is possible to cause the shutter of the X-ray source to also serve as the shielding portion, it is possible to simplify the configuration of the microcrystal structure analysis apparatus.

Preferably, each time the sample is rotated a predetermined number of times, the sample drive unit stops the rotation for a predetermined time period, and a magnetic field direction of the magnetic field is adjustable such that the specific part is directed in the desired direction when the sample drive unit stops the rotation of the sample.

In this case, by adjusting the magnetic field direction of the magnetic field, it is possible to direct the specific part of the sample in the desired direction when the sample drive unit stops rotation of the sample. In this state, the shielding portion is switched to the permitting position by the shielding control unit, and thus the X rays are applied to the sample while the rotation of the sample is stopped. Therefore, as compared to the case where the X rays are applied to the sample while the sample is rotated, it is possible to increase the application time per unit time, and thus it is possible to obtain a favorable X-ray diffraction image in a further short time.

The state switching device is preferably composed of an X-ray detection control unit configured to control X-ray detection of the X-ray detection unit such that X-ray detection of the X-ray detection unit is disenabled when the specific part is not directed in a desired direction; and X-ray detection of the X-ray detection unit is permitted when the specific part is directed in the desired direction.

In this case, since it is unnecessary to provide the shielding portion or the shutter which shields application of the X rays, it is possible to simplify the configuration of the microcrystal structure analysis apparatus.

Preferably, a plurality of the specific parts are set along a rotation direction of the sample, the state switching device is composed of an X-ray detection control unit configured to control X-ray detection of the X-ray detection unit such that X-ray detection of the X-ray detection unit is disenabled when none of the plurality of the specific parts are directed in a desired direction; and X-ray detection of the X-ray detection unit is permitted when any of the plurality of the specific parts is directed in the desired direction, and the microcrystal structure analysis apparatus further includes: a storage unit having a plurality of storage areas configured to store an X-ray diffraction image obtained from the X rays detected by the X-ray detection unit, for each specific part; and a storage control unit configured to, each time the X-ray detection unit detects the X rays through each specific part, store an X-ray diffraction image obtained from the X rays into the storage area, for the corresponding specific part, of the storage unit.

In this case, it is possible to obtain X-ray diffraction images of the plurality of the specific parts while the sample makes one rotation, and thus it is possible to efficiently perform X-ray structure analysis.

An X-ray shielding device according to another aspect of the present invention is an X-ray shielding device provided in a microcrystal structure analysis apparatus including: a magnetic field generation unit; a sample drive unit configured to rotate a sample having microcrystals suspended therein relative to the magnetic field generation unit such that a temporally varying magnetic field is applied to the sample to three-dimensionally orient the microcrystals; an X-ray source configured to apply X rays to the sample that is being rotated by the sample drive unit; and an X-ray detection unit capable of detecting the X rays that have passed through and have been diffracted by the sample. Preferably, the X-ray shielding device includes: a shielding portion switchable between a shielding position where the shielding portion shields application of the X rays and a permitting position where the shielding portion permits application of the X rays; a shielding drive unit configured to switching-drive the shielding portion; and a shielding control unit configured to control switching-driving of the shielding drive unit such that the shielding portion is located at the shielding position when a specific part which is a part of the sample in a rotation direction thereof is not directed in a desired direction; and the shielding portion is located at the permitting position when the specific part is directed in the desired direction, the shielding portion includes a shielding portion main body formed in a disc shape and configured to shield application of the X rays at one surface thereof; and a slit formed in the shielding portion main body and configured to permit application of the X rays by causing the X rays to pass therethrough, the shielding drive unit is capable of rotary-driving the shielding portion main body about an axis thereof, and the shielding control unit controls driving of the shielding drive unit such that rotation of the shielding portion main body is synchronized with rotation of the sample.

According to the present invention, the same advantageous effects as those of the above-described microcrystal structure analysis apparatus are provided. In addition, the X-ray shielding device only needs to be arranged on a path in the microcrystal structure analysis apparatus on which path the X rays are applied, and thus it is possible to easily mount the X-ray shielding device on an existing microcrystal structure analysis apparatus.

Advantageous Effects of Invention

According to the present invention, it is possible to obtain a favorable X-ray diffraction image even when X rays are applied to a pseudo-single-crystallized sample while the sample is rotated.

BRIEF DESCRIPTION OF DRAWINGS

FIG. 9 is a photograph substituted for drawing, showing an X-ray diffraction image of a pseudo-single-crystallized sample obtained by the microcrystal structure analysis apparatus with using an X-ray shielding device.

In FIG. 13, (a) is an enlarged view of a sample container shown in FIG. 11, and (b) is an enlarged view of the sample container showing a state where a magnetic field direction of a time-varying magnetic field is adjusted.

DESCRIPTION OF EMBODIMENTS

Hereinafter, embodiments of the present invention will be described with reference to the drawings.

Figure 1:
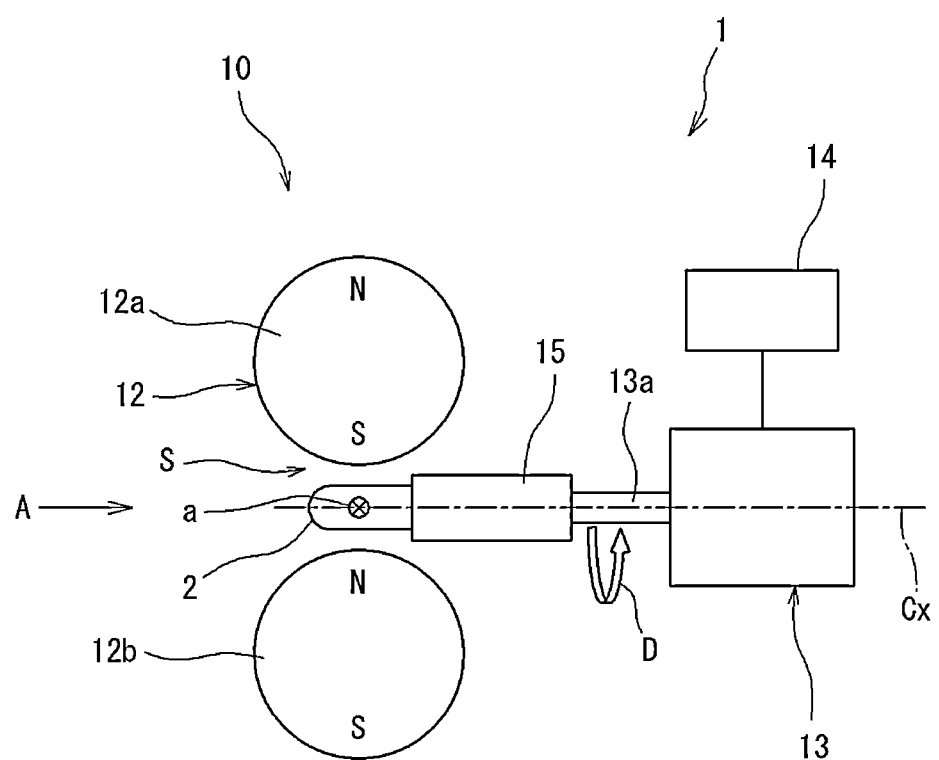
FIG. 1 is a schematic configuration diagram showing a microcrystal structure analysis apparatus according to a first embodiment of the present invention.

FIG. 1 is a schematic configuration diagram showing a microcrystal structure analysis apparatus according to a first embodiment of the present invention. In FIG. 1, the microcrystal structure analysis apparatus 1 includes a microcrystal orientation device 10 which applies a temporally varying magnetic field (hereinafter, referred to as time-varying magnetic field) to a sample container 2 placed at a predetermined position. The sample container 2 is formed, for example, in a bottomed cylindrical shape, and contains a sample having suspended therein microcrystals 3 (see FIG. 2) such as an organic compound, an inorganic compound, a biological material, or the like in the field of medicine, the field of biotechnology, the field of polymeric materials, or the like.

Figure 2:
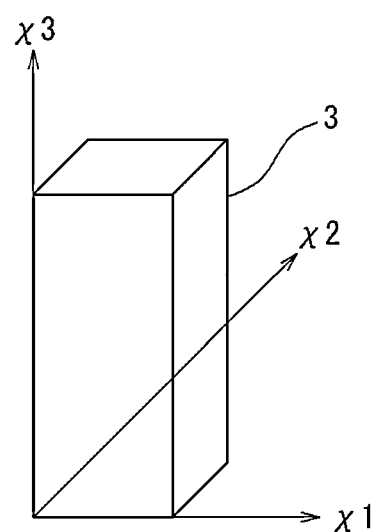
FIG. 2 is a perspective view showing magnetization axes of a microcrystal.

The microcrystals 3 are composed of biaxial crystals whose magnetic susceptibilities in mutually orthogonal three directions are different from each other, and have magnetically biaxial anisotropy. FIG. 2 is a perspective view showing magnetization axes of the microcrystal 3. As shown in FIG. 2, each microcrystal 3 has different magnetic susceptibilities $\chi_1$, $\chi_2$, and $\chi_3$ in the direction of the three axes, respectively, and a magnitude relation of $\chi_1 > \chi_2 > \chi_3$ is established. Hereinafter, the axis for the magnetic susceptibility $\chi_1$ is referred to as a magnetization-easy axis, the axis for the magnetic susceptibility $\chi_2$ is referred to as an intermediate axis, and the axis for the magnetic susceptibility $\chi_3$ is referred to as a magnetization-difficult axis.

In FIG. 1, the microcrystal orientation device 10 includes a magnetic field generation unit 12, a sample drive unit 13 which rotates the sample container 2 relative to the magnetic field generation unit 12, and a sample control unit 14 which controls driving of the sample drive unit 13.

The magnetic field generation unit 12 includes a pair of upper and lower permanent magnets 12a, 12b fixed to a casing (not shown). The permanent magnets 12a, 12b are each formed in a spherical shape and are arranged such that the north pole and the south pole thereof are opposed to each other. A space S for placing the sample container 2 is formed between these permanent magnets 12a, 12b.

The sample drive unit 13 is composed of, for example, a stepping motor, and a chuck 15 which holds the sample container 2 is mounted at a leading end of an output shaft 13a of the sample drive unit 13. Thus, when the sample drive unit 13 is driven, the sample container 2 is rotated relative to the fixed magnetic field generation unit 12 in one direction (the direction of an arrow D) via the output shaft 13a and the chuck 15. At that time, the rotation speed of the sample container 2 is set to a speed required for forming a rotating magnetic field.

The sample control unit 14 controls driving of the sample drive unit 13 such that each time the sample container 2 is rotated by substantially 180×n degrees (n is an arbitrary natural number), the rotation is temporarily substantially stopped for a predetermined time period $t_s$ is required for forming a static magnetic field. At that time, the sample container 2 is rotated by substantially 180×n degrees in a predetermined time period $t_r$. Here, in the present specification, the meaning of "substantially stopped" includes not only a state of being completely stopped but also a state of being locally slowly rotated such that a static magnetic field is practically formed.

Figure 3:
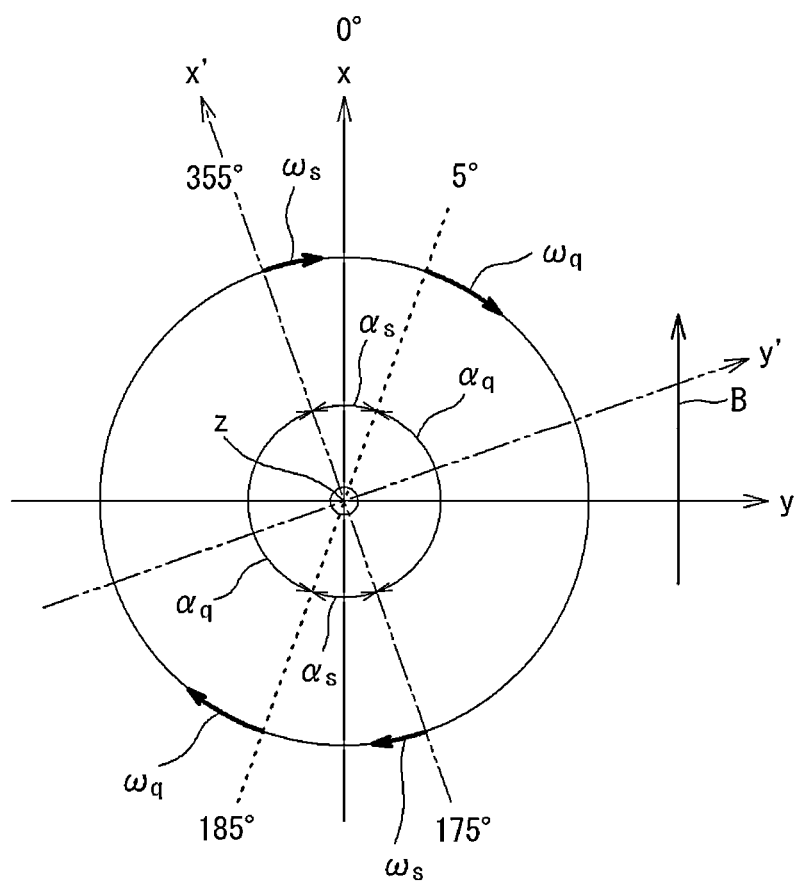
FIG. 3 is a schematic diagram showing a method for controlling a sample drive unit by a sample control unit.

FIG. 3 is a schematic diagram showing a method for controlling the sample drive unit 13 by the sample control unit 14. In the present embodiment, as shown in FIG. 3, a time-varying magnetic field is applied on an xy plane by the sample control unit 14. Hereinafter, the case will be described in which, for example, an x axis at the upper side in the sheet surface of FIG. 3 as seen from a z axis is defined as a reference (0 degree) and the sample container 2 is rotated about the z axis in a clockwise direction in FIG. 3. It should be noted that the x axis is laid parallel to a magnetic field direction B.

First, in a range of 170 degrees (a rotation angle $\alpha q$) from a position of 5 degrees to a position of 175 degrees including a y axis, the sample container 2 is high-speed rotated at a predetermined angular speed $\omega q$ (e.g., 25 rpm). Then, in a range of 10 degrees (a rotation angle $\alpha s$) from the position of 175 degrees to a position of 185 degrees including the x axis, the sample container 2 is low-speed rotated at a predetermined angular speed $\omega s$ (e.g., 5 rpm) to come into a substantially stopped state.

Thereafter, in a range of 170 degrees (a rotation angle $\alpha q$) from the position of 185 degrees to a position of 355 degrees including the y axis, the sample container 2 is high-speed rotated at the angular speed $\omega q$. Furthermore, in a range of 10 degrees (a rotation angle $\alpha s$) from the position of 355 degrees to the position of 5 degrees (365 degrees) including the x axis, the sample container 2 is low-speed rotated at the angular speed $\omega s$ to come into a substantially stopped state. By controlling driving of the sample drive unit 13 by the sample control unit 14 such that each time the sample container 2 is high-speed rotated by 170 degrees, the sample container 2 is temporally low-speed rotated (substantially stopped) as described above, the time-varying magnetic field is applied.

Figure 4:
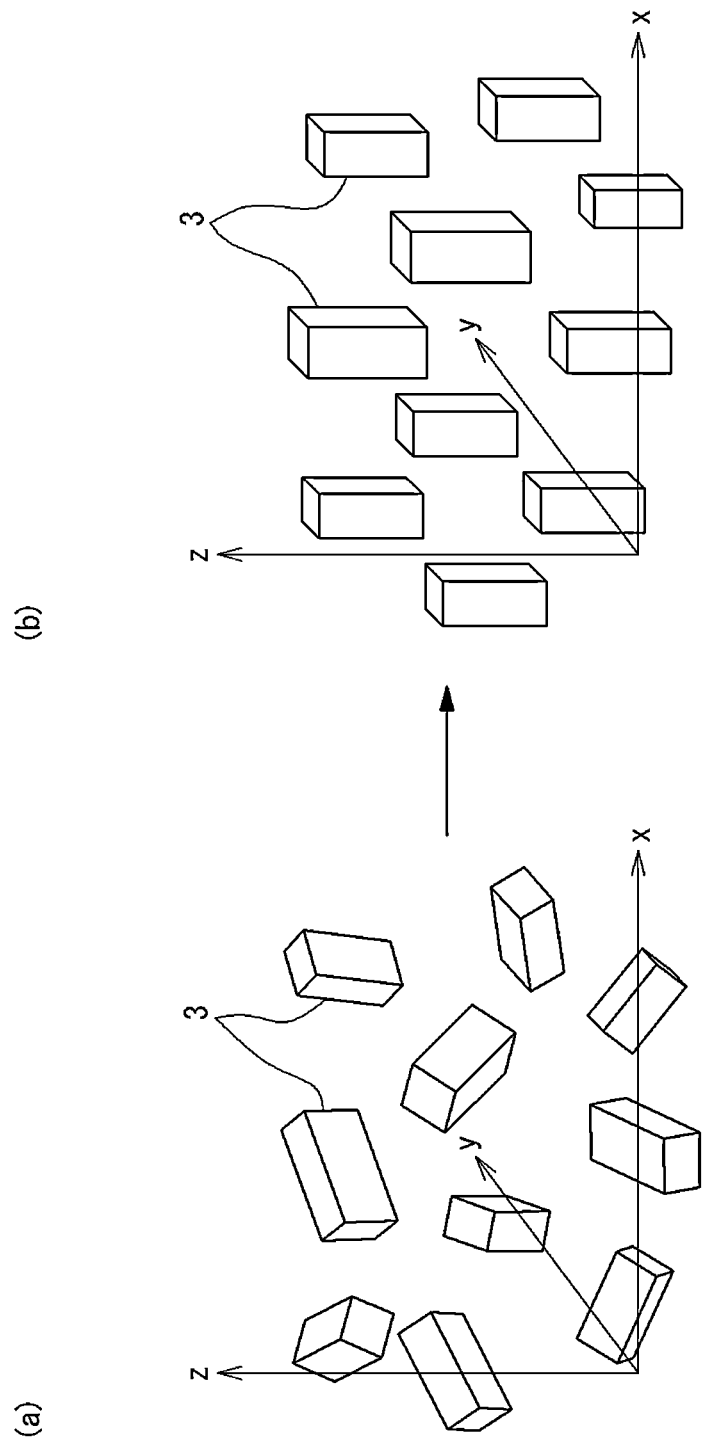
FIG. 4 is a perspective view explaining three-dimensional orientation of microcrystals.

When the time-varying magnetic field is applied as described above, due to a rotating magnetic field being formed during high-speed rotation, the magnetization-difficult axes of the microcrystals 3 suspended within the sample container 2 are oriented in a z axis direction perpendicular to the xy plane (the plane of rotation). Then, due to a static magnetic field being formed during low-speed rotation, the magnetization-easy axis of each microcrystal 3 is oriented parallel to the direction of an x' axis for an x'y' rotational coordinate rotated with the sample container 2, and the other axis thereof is also automatically oriented parallel to the direction of a y' axis therefor. Thus, the microcrystals 3 come from a state of being randomly arranged as shown in (a) of FIG. 4 into a state of being three-dimensionally oriented as shown in (b) of FIG. 4, namely, a state of being pseudo-single-crystallized.

Figure 5:
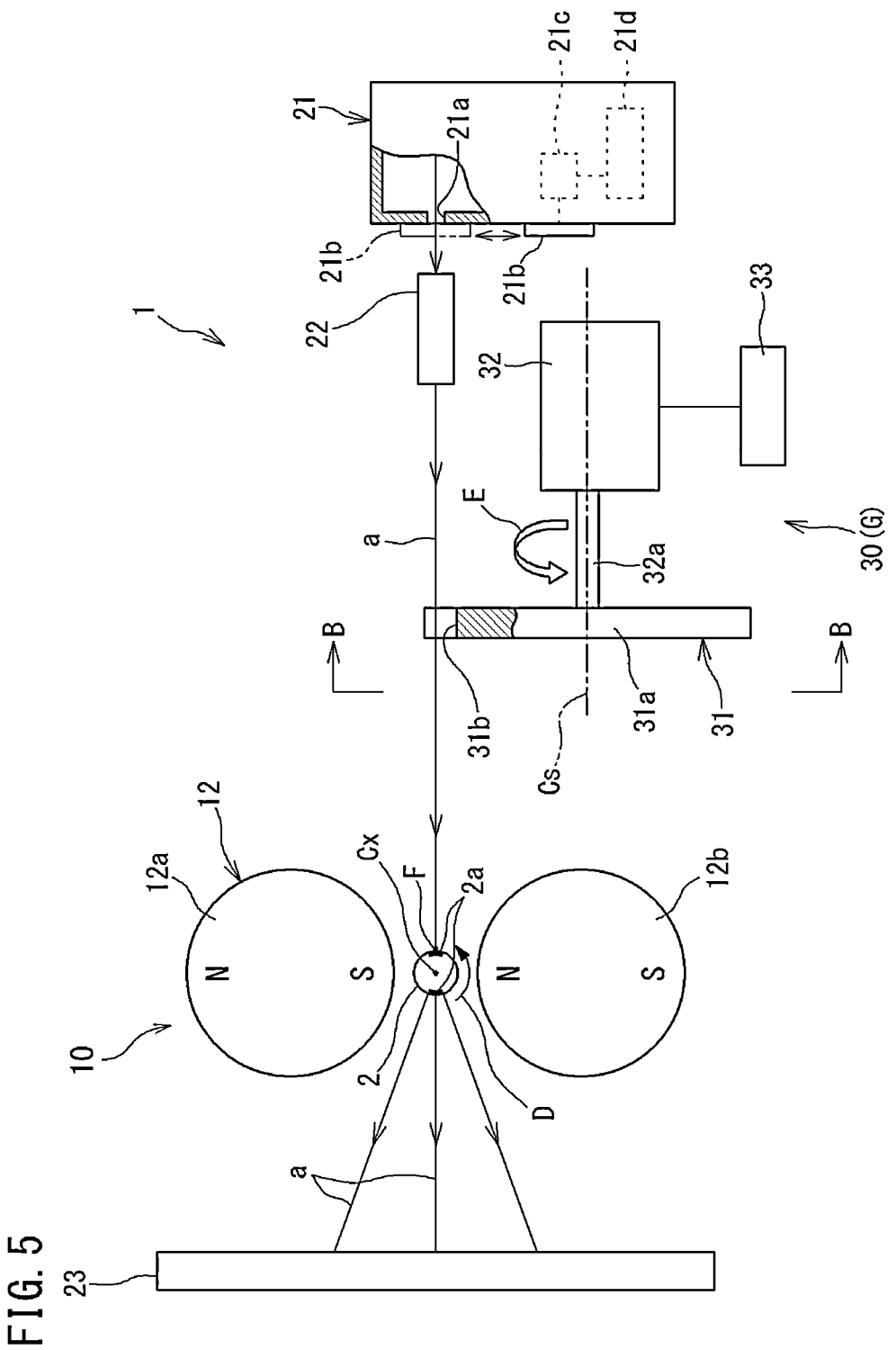
FIG. 5 is a view as seen from the direction of an arrow A in FIG. 1, showing a state where X rays are applied to a sample container.

In FIG. 1, in order to perform X-ray structure analysis in a state where the microcrystals 3 are pseudo-single-crystallized, the microcrystal structure analysis apparatus 1 is configured to apply X rays a to the sample container 2 in a direction perpendicular to the sheet surface of FIG. 1 while rotating the sample container 2. FIG. 5 is a view as seen from the direction of an arrow A in FIG. 1, showing a state where the X rays a are applied to the sample container 2. In FIG. 5, the microcrystal structure analysis apparatus 1 includes an X-ray source 21 which applies the X rays a to the sample container 2; and an X-ray detection unit 23 which detects the X rays a that have passed through and have been diffracted by the sample container 2. The X-ray detection unit 23 is composed of, for example, an imaging plate.

As shown in FIG. 5, the X-ray source 21 includes an X-ray window portion 21*a* for emitting the generated X rays a toward the sample container 2; a shutter 21*b* which opens and closes the X-ray window portion 21*a*; a shutter drive unit 21*c* which drives opening and closing of the shutter 21*b*; and a shutter control unit 21*d* which controls driving of the shutter drive unit 21*c*.

The shutter 21*b* is arranged outside the X-ray window portion 21*a* so as to be capable of reciprocating in an up-down direction. Specifically, the shutter 21*b* is arranged so as to be capable of reciprocating between a closing position where the shutter 21*b* closes the X-ray window portion 21*a* to block emission of the X rays a (a position shown by an alternate long and two short dashes line in the drawing) and an opening position where the shutter 21*b* opens the X-ray window portion 21*a* to permit emission of the X rays a (a position shown by a solid line in the drawing).

The shutter drive unit 21*c* is composed of, for example, a rotary solenoid, and the shutter 21*b* reciprocates in the up-down direction by driving the rotary solenoid. The shutter control unit 21*d* controls driving of the shutter drive unit 21*c* such that: the shutter 21*b* is located at the opening position when X-ray structure analysis is started; and the shutter 21*b* is located at the closing position when the X-ray structure analysis is ended.

The X rays a emitted from the X-ray source 21 pass through a collimator 22 and are applied to the sample container 2 that is being rotated in a state of being held by the sample drive unit 13, from a direction substantially perpendicular to a rotation axis $C_x$ of the sample container 2. Then, the X rays a that have passed through and have been diffracted by the sample container 2 are detected by the X-ray detection unit 23, whereby it is possible to obtain an X-ray diffraction image.

Figure 6:
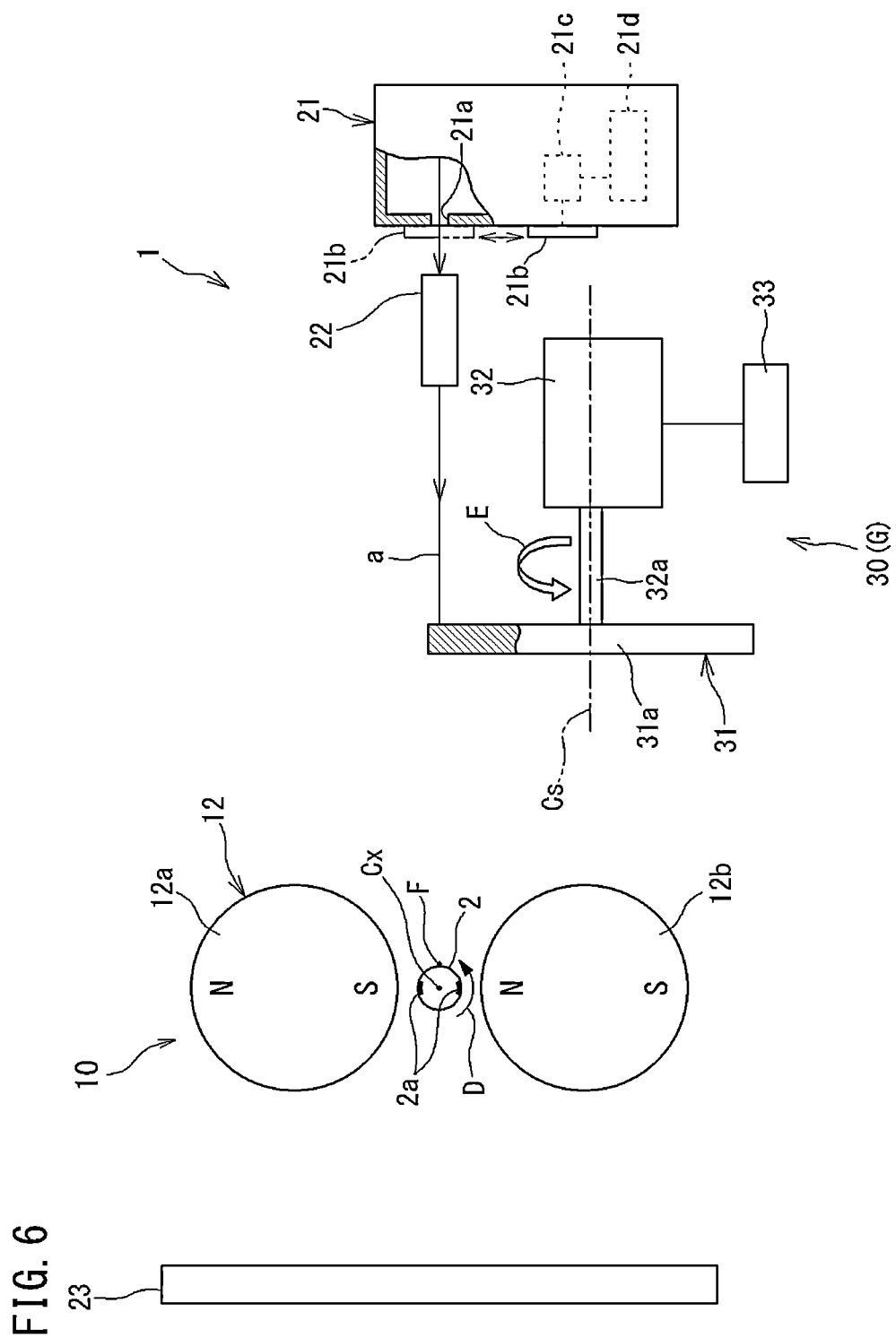
FIG. 6 is a view as seen from the direction of the arrow A in FIG. 1, showing a state where application of the X rays to the sample container is shielded.

The microcrystal structure analysis apparatus 1 further includes an X-ray shielding device 30 which intermittently shields emission of the X rays a. FIG. 6 is view as seen from the direction of the arrow A in FIG. 1, showing a state where application of the X rays a to the sample container 2 is shielded by the X-ray shielding device 30. In FIGS. 5 and 6, the X-ray shielding device 30 includes: a shielding portion 31 which is switchable between a shielding position (see FIG. 6) where the shielding portion 31 shields application of the X rays a and a permitting position (see FIG. 5) where the shielding portion 31 permits application of the X rays a; a shielding drive unit 32 which switch-drives the shielding portion 31; and a shielding control unit 33 which controls driving of the shielding drive unit 32 in synchronization with rotation of the sample container 2.

Figure 7:
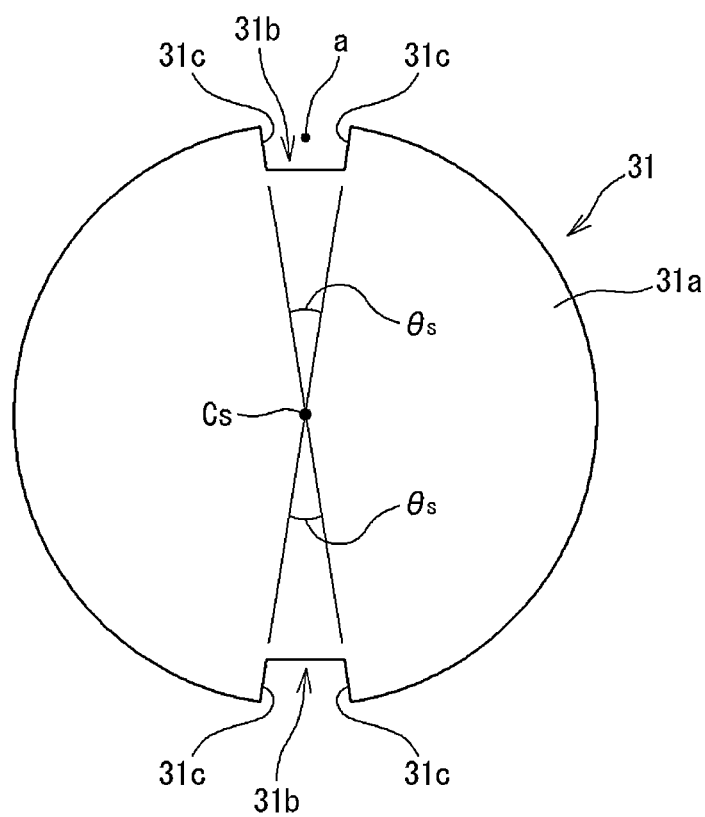
FIG. 7 is a view as seen from the direction of arrows B in FIG. 5.

The shielding portion 31 is arranged between the sample container 2 held by the sample drive unit 13 and the X-ray source 21 so as to be rotatable in one direction (the direction of an arrow E). FIG. 7 is a view as seen from the direction of arrows B in FIG. 5, showing a front view of the shielding portion 31. In FIG. 7, the shielding portion 31 includes: a shielding portion main body 31*a* which is formed, for example, from a lead material in a disc shape and shields application of the X rays a at one surface thereof (at the right side in FIG. 6); and a pair of slits 31*b* which are formed in an outer peripheral portion of the shielding portion main body 31*a* and permit application of the X rays a to the sample container 2 by causing the X rays a to pass therethrough. A rotation axis $C_s$ of the shielding portion main body 31*a* is laid substantially perpendicular to the rotation axis $C_x$ of the sample container 2.

The slits 31*b* are each composed of a recessed groove and formed at two locations in a circumferential direction on the outer peripheral portion of the shielding portion main body 31*a* with an angle difference of substantially 180 degrees therebetween. In addition, side surfaces 31*c* of each slit 31*b* at both sides in the circumferential direction are formed so as to extend outward in a radial direction with the rotation axis $C_s$ of the shielding portion main body 31*a* as a center, and the angle $\theta_s$ formed between both side surfaces 31*c* is set to the same angle as a predetermined angle $\theta_{xn}$ of a later-described specific part 2*a* of the sample container 2. Thus, when the shielding portion main body 31*a* is rotated about the rotation axis $C_s$ in one direction, the shielding portion 31 is alternately switched between a rotational position (the shielding position) where the X rays a are shielded by the shielding portion main body 31*a* and a rotational position (the permitting position) where the X rays a pass through the slit 31*b*.

In FIGS. 5 and 6, the shielding drive unit 32 is composed of, for example, a stepping motor, and a center portion of the shielding portion main body 31*a* is attached to a leading end of an output shaft 32*a* of the shielding drive unit 32. Therefore, it is possible to rotate the shielding portion 31 about the rotation axis $C_s$ via the output shaft 32*a* by driving the shielding drive unit 32.

Figure 8:
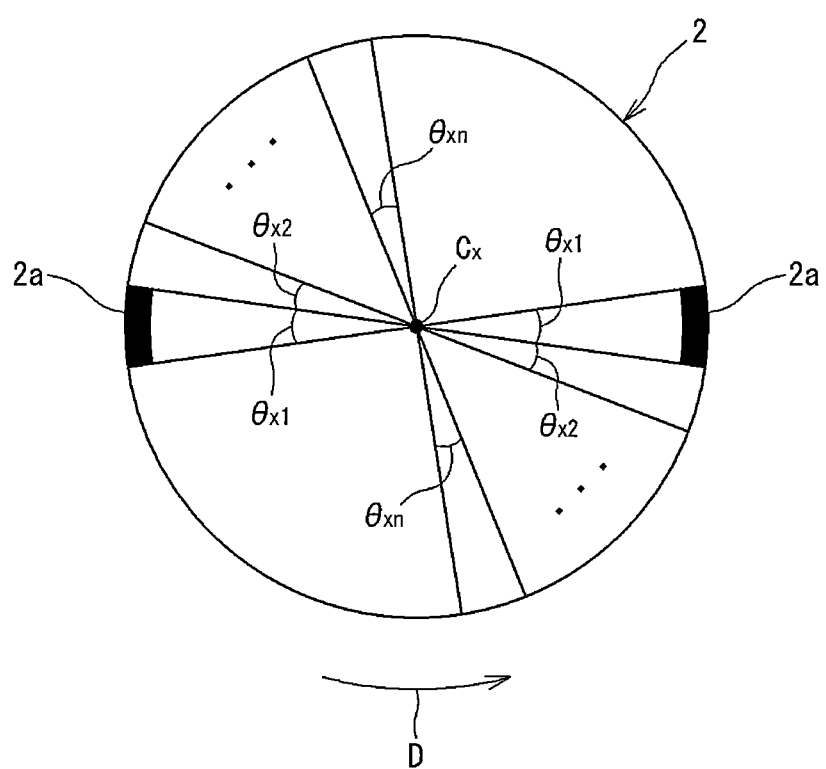
FIG. 8 is an enlarged view of the sample container shown in FIG. 5.

FIG. 8 is an enlarged view showing the sample container 2 in FIG. 5. In FIG. 8, specific parts 2*a* to which the X rays a are applied are set in parts, in the circumferential direction (rotation direction), of an outer periphery of the sample container 2. In the present embodiment, for the microcrystals 3 pseudo-single-crystallized within the sample container 2, an X-ray diffraction image obtained by applying the X rays a in a state before the sample container 2 is rotated by 180 degrees and an X-ray diffraction image obtained by applying the X rays a in a state after the sample container 2 is rotated by 180 degrees, are the same. Therefore, the specific parts 2*a* in the present embodiment are set at two locations on the outer peripheral portion of the sample container 2 with an angle difference of substantially 180 degrees therebetween.

In addition, each specific part 2*a* is set at a predetermined angle $\theta_{x1}$ (e.g., 10 degrees) centered at the rotation axis $C_x$. After the X rays a are applied at the predetermined angle $\theta_{x1}$ and an X-ray diffraction image is obtained, each specific part 2*a* is newly set at an angle $\theta_{x2}$ which is adjacent to and the same as the predetermined angle $\theta_{x1}$. By repeating resetting of the specific parts 2*a* as described above, it is possible to obtain a plurality of (n) X-ray diffraction images for a predetermined angle range ($\theta_{x1} + \theta_{x2} + \ldots + \theta_{xn}$) centered at the rotation axis $C_x$.

The shielding control unit 33 controls rotary driving of the shielding drive unit 32 such that: the shielding portion 31 is located at the shielding position to shield application of the X rays a (see FIG. 6) when none of the specific parts 2*a* are directed in a desired direction; and the shielding portion 31 is located at the permitting position to permit application of the X rays a (see FIG. 5) when any specific part 2a is directed in the desired direction.

Therefore, the X-ray shielding device 30 in the present embodiment is configured as a state switching device G which switches between a state where detection of the X rays a by the X-ray detection unit 23 is disenabled and a state where detection of the X rays a by the X-ray detection unit 23 is enabled, in accordance with a rotational position of each specific part 2a.

The desired direction is set to an arbitrary direction as appropriate. For example, in the present embodiment, a state where any specific part 2a is directed in the desired direction is defined as a state where the specific part 2a is located at an application position F at which the X rays a are applied to the sample container 2 and is directed toward the X-ray source 21.

The shielding control unit 33 controls rotary driving of the shielding drive unit 32 such that rotation of the shielding portion 31 is synchronized with rotation of the sample container 2. In other words, the shielding control unit 33 controls rotary driving of the shielding drive unit 32 such that: when the sample container 2 is high-speed rotated, the shielding portion 31 is high-speed rotated at the same angular speed ωq as that of the sample container 2; and when the sample container 2 is low-speed rotated, the shielding portion 31 is low-speed rotated at the same angular speed ωs as that of the sample container 2.

Therefore, when each specific part 2a of the sample container 2 is set and the shielding portion 31 is rotated as described above, a rotation start position of the shielding portion 31 may be previously set such that as shown in FIG. 5, in a state where any specific part 2a of the sample container 2 is directed in the desired direction, namely, when the specific part 2a is present at the application position F of the X rays a, any slit 31b of the shielding portion 31 is located at a rotational position where the X rays a are caused to pass therethrough. By so setting, after the shielding portion 31 is rotated in synchronization with the sample container 2, each time any specific part 2a is located at a rotational position that coincides with the application position F of the X rays a, any slit 31b of the shielding portion 31 is located at the rotational position where the X rays a are caused to pass therethrough.

Thus, in a state where any specific part 2a of the sample container 2 is directed in the desired direction, the X rays a are intermittently applied to the sample container 2. Therefore, the X rays a are intermittently applied to the sample container 2 for a predetermined time period $t_x$ (e.g., 5 minutes), and the X rays a that have passed through and have been diffracted by the sample container 2 are detected by the X-ray detection unit 23, whereby it is possible to obtain an X-ray diffraction image of the pseudo-single-crystallized sample.

According to the microcrystal structure analysis apparatus 1 and the microcrystal structure analysis method of the present embodiment described above, when the sample container 2 in which the microcrystals 3 are suspended is rotated relative to the magnetic field generation unit 12, the microcrystals 3 are three-dimensionally oriented (pseudo-single-crystallized). Then, the X rays a are applied to the sample container 2 while the rotation is continued, and the X rays a that have passed through and have been diffracted by the sample container 2 are detected, whereby it is possible to obtain an X-ray diffraction image of the pseudo-single-crystallized sample. At that time, only when any specific part 2a of the sample container 2 is directed in the desired direction, application of the X rays a is permitted by switching the shielding portion 31 from the shielding position to the permitting position, and thus it is possible to intermittently apply the X rays a to the sample container 2 in a state where the specific part 2a is directed in the desired direction. Therefore, it is possible to obtain a favorable X-ray diffraction image even when the X rays a are applied to the pseudo-single-crystallized sample while the sample is rotated.

In addition, before the disc-shaped shielding portion main body 31a is rotary-driven by the shielding drive unit 32, the rotation start position of the shielding portion main body 31a is previously set such that only when any specific part 2a of the sample container 2 is directed in the desired direction, any slit 31b of the shielding portion 31 is located at a rotational position where the X rays a are caused to pass therethrough. If so setting, by rotating the shielding portion main body 31a in synchronization with rotation of the sample container 2, it is possible to apply the X rays a only when any specific part 2a of the sample container 2 is directed in the desired direction. Therefore, it is possible to intermittently apply the X rays a to the sample in a state where any specific part is directed in the desired direction, and thus it is possible to obtain a favorable X-ray diffraction image with a simple configuration.

In addition, since the slits 31b of the shielding portion 31 are formed at two locations in the circumferential direction on the shielding portion main body 31a with an angle difference of substantially 180 degrees therebetween, it is possible to apply the X rays a to the sample container 2 twice by causing the X rays a to pass through the respective two slits 31b while the shielding portion main body 31a makes one rotation. Thus, as compared to the case where the slit 31b is formed at only one location, it is possible to increase the application time per one rotation of the shielding portion main body 31a. Therefore, when an X-ray diffraction image obtained by applying the X rays a in a state before the sample container 2 is rotated by 180 degrees and an X-ray diffraction image obtained by applying the X rays a in a state after the sample container 2 is rotated by 180 degrees are the same, it is possible to obtain a favorable X-ray diffraction image in a short time.

Moreover, since the shielding portion 31 is arranged between the X-ray source 21 and the sample container 2, the shielding portion 31 shields and permits application of the X rays a that have not been scattered. Therefore, as compared to the case where the shielding portion 31 is arranged between the sample container 2 and the X-ray detection unit 23, namely, the case where the shielding portion 31 is arranged so as to shield and permit application of the X rays a (see FIG. 5) that have been scattered, it is possible to reduce the size of the shielding portion 31.

Furthermore, the X-ray shielding device 30 only needs to be arranged on a path in the microcrystal structure analysis apparatus 1 on which path the X rays a are applied, and thus it is possible to easily mount the X-ray shielding device 30 on an existing microcrystal structure analysis apparatus.

FIG. 9 is a photograph substituted for drawing, showing an X-ray diffraction image of a pseudo-single-crystallized sample obtained by the microcrystal structure analysis apparatus of the present invention with using the X-ray shielding device. Specifically, (a) of FIG. 9 is an X-ray diffraction image obtained when each specific part is set at an arbitrary angle of 10 degrees which is a part in the circumferential direction of a sample container, and (b) of FIG. 9 is an X-ray diffraction image obtained when each specific part is set at an angle of 10 degrees which is different from the angle range in (a) of FIG. 9. The sample within the sample container is a suspension obtained by incorporating about 10 wt % of microcrystals (particle size <80 μm) of L-alanine into an ultraviolet-curable monomer which is a suspending medium.

Figure 10:
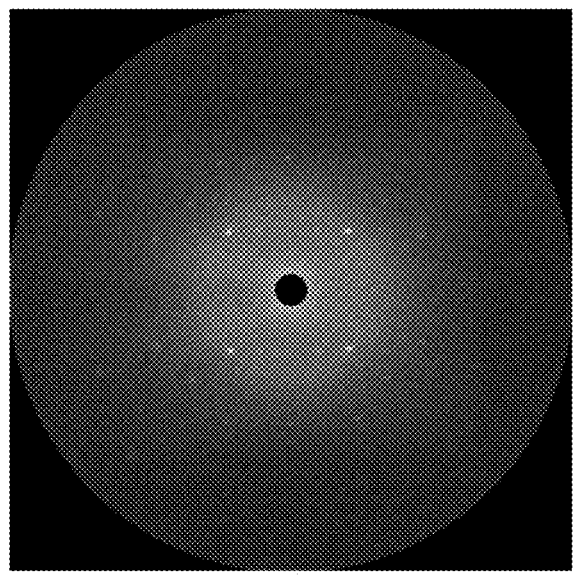
FIG. 10 is a photograph substituted for drawing, showing an X-ray diffraction image of a pseudo-single-crystallized sample obtained by the microcrystal structure analysis apparatus without using the X-ray shielding device.

FIG. 10 is a photograph substituted for drawing, showing an X-ray diffraction image of a pseudo-single-crystallized sample obtained by the microcrystal structure analysis apparatus of the present invention without using the X-ray shielding device. In the microcrystal structure analysis apparatus used in FIG. 10, since X rays are applied to the rotating sample at all times, the X rays are applied to each rotational position over the entire circumference of the sample. Thus, in the X-ray diffraction image in FIG. 10, all diffraction spots (white points in the drawing) obtained by diffraction at respective rotational positions over the entire circumference of the sample are observed. On the other hand, when the respective X-ray diffraction images obtained with using the X-ray shielding device in (a) and (b) of FIG. 9 are compared, it is recognized that the positions of observed diffraction spots are different and only a diffraction spot corresponding to each specific part of the sample is observed. In other words, it is recognized that when the X-ray shielding device of the present invention is used, a favorable X-ray diffraction image is obtained for a pseudo-single-crystallized sample.

Figure 11:
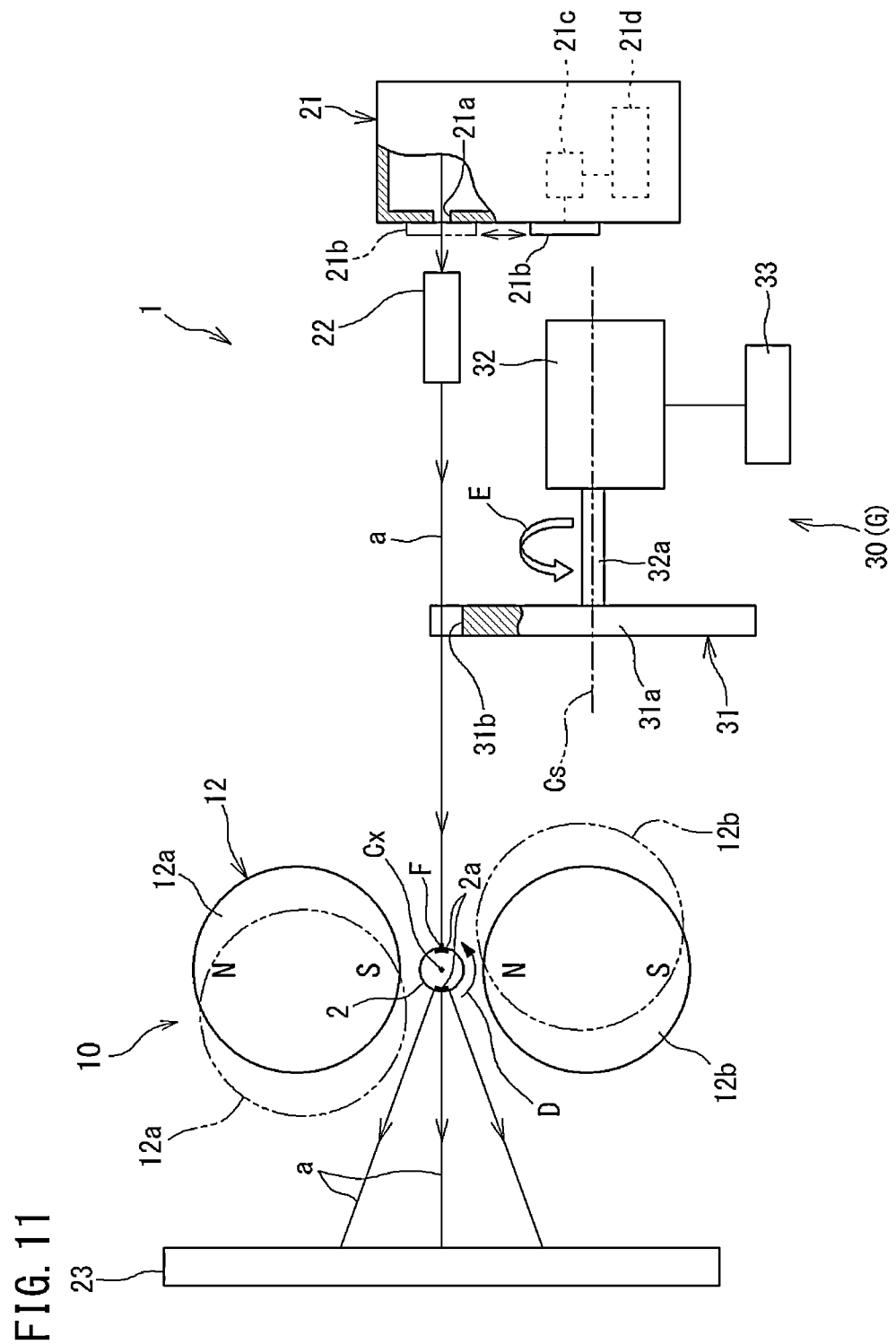
FIG. 11 is a schematic configuration diagram showing a microcrystal structure analysis apparatus according to a second embodiment of the present invention.
Figure 12:
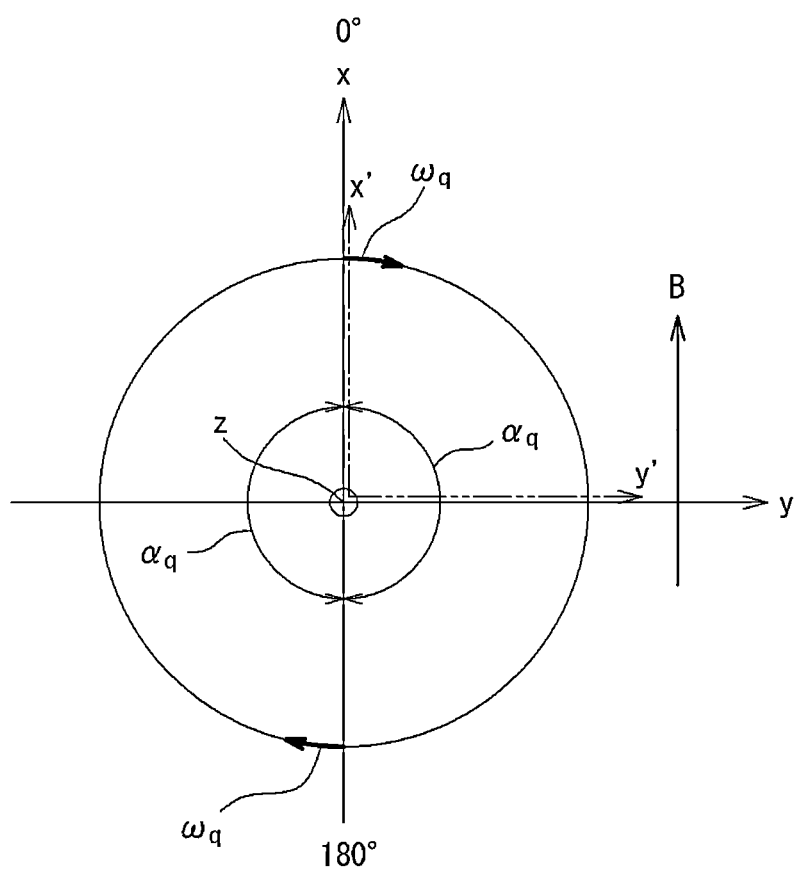
FIG. 12 is a schematic diagram showing a method for controlling a sample drive unit by a sample control unit in the microcrystal structure analysis apparatus in FIG. 11.

FIG. 11 is a schematic configuration diagram showing a microcrystal structure analysis apparatus 1 according to a second embodiment of the present invention. In addition, FIG. 12 is a schematic diagram showing a method for controlling the sample drive unit 13 by the sample control unit 14 in the microcrystal orientation device 10 of the microcrystal structure analysis apparatus 1. The microcrystal structure analysis apparatus 1 of the present embodiment is different from that of the first embodiment in that the method for controlling driving of the sample drive unit 13 and the configuration of the magnetic field generation unit 12 in the microcrystal orientation device 10 are different.

In FIG. 12, the sample control unit 14 in the microcrystal orientation device 10 of the present embodiment controls driving of the sample drive unit 13 such that each time the sample container 2 is rotated a predetermined number of times, the rotation is stopped for a predetermined time period. In other words, in forming a static magnetic field, the sample control unit 14 causes the sample container 2 to come into a substantially stopped state by completely stopping the sample container 2, not by rotating the sample container 2 at a low speed. Hereinafter, the control method by the sample control unit 14 will be described with the case where, for example, an x axis at the upper side in the sheet surface of FIG. 12 as seen from a z axis is defined as a reference (0 degree) and the sample container 2 is rotated about the z axis in a clockwise direction in FIG. 12.

First, in a range of 180 degrees (a rotation angle αq) from a position of 0 degree to a position of 180 degrees including a y axis, the sample container 2 is rotated at a predetermined angular speed ωq (e.g., 25 rpm). Then, at the position of 180 degrees on the x axis, the sample container 2 is completely stopped for a predetermined time period $t_s$ (e.g., 1 second).

Thereafter, in a range of 180 degrees (a rotation angle αq) from the position of 180 degrees to the position of 0 degree (360 degrees) including the y axis, the sample container 2 is rotated at the angular speed ωq again. Then, on the x axis which is the position of 0 degree, the sample container 2 is completely stopped for a predetermined time period $t_s$ (e.g., 1 second). By the sample control unit 14 controlling driving of the sample drive unit 13 such that each time the sample container 2 is rotated by 180 degrees, the rotation is temporarily stopped as described above, a time-varying magnetic field is applied.

When the time-varying magnetic field is applied as described above, due to a rotating magnetic field being formed during rotation, the magnetization-difficult axes of the microcrystals 3 suspended within the sample container 2 are oriented in a z axis direction perpendicular to an xy plane (the plane of rotation). Then, due to a static magnetic field being formed during stop, the magnetization-easy axis of each microcrystal 3 is oriented parallel to the direction of an x' axis for an x'y' rotational coordinate rotated with the sample container 2, and the other axis thereof is also automatically oriented parallel to the direction of a y' axis therefor. Thus, the microcrystals 3 come from a state of being randomly arranged (see (a) of FIG. 4) into a state of being three-dimensionally oriented (see (b) of FIG. 4), namely, a state of being pseudo-single-crystallized.

It should be noted that in the present embodiment, rotation is substantially stopped every substantially 180 degrees, but rotation may be substantially stopped every a plurality of rotations such a 360 degrees (one rotation), 540 degrees (one and half rotation), or the like, or may be substantially stopped at a different rotation angle each time. In short, when rotation is made by arbitrary natural number times that of substantially 180 degrees, the rotation may be substantially stopped.

In FIG. 11, the microcrystal structure analysis apparatus 1 of the present embodiment is able to adjust a magnetic field direction B (see (a) and (b) of FIG. 13) of the time-varying magnetic field. Specifically, the permanent magnets 12a, 12b of the magnetic field generation unit 12 are rotatable about the rotation axis $C_x$ of the sample container 2 and held at predetermined rotational positions. Thus, by rotating the permanent magnets 12a, 12b to adjust the magnetic field direction B of the time-varying magnetic field, in applying the X rays a to the sample container 2, it is possible to direct any specific part 2a of the sample container 2 in a desired direction when rotation of the sample container 2 is stopped. Hereafter, a method for adjusting the magnetic field direction B of the time-varying magnetic field will be described.

In FIG. 13, (a) is an enlarged view of the sample container 2 shown in FIG. 11, and (b) is an enlarged view of the sample container 2 showing a state where the magnetic field direction B of the time-varying magnetic field is adjusted. In (a) of FIG. 13, the permanent magnets 12a, 12b of the magnetic field generation unit 12 are held at such rotational positions as to provide a state where the magnetic field direction B is directed vertically upward. In this state, when rotation of the sample container 2 is stopped, if a predetermined angle $\theta_{x1}$ present at the application position F of the X rays a and a predetermined angle $\theta_{x1}$ present at a position having an angle difference of 180 degrees from the application position F are set as specific parts 2a of the sample container 2, it is possible to cause any of the respective specific parts 2a of the sample container 2 to be present at the application position F of the X rays a each time the sample container 2 is rotated by 180 degrees and stopped.

After the X rays a are applied to the specific part 2a at the predetermined angle $\theta_{x1}$ and an X-ray diffraction image is obtained, as shown in (b) of FIG. 13, similarly to the first embodiment, each specific part 2a is newly set at an angle $\theta_{x2}$ which is adjacent to and the same as the predetermined angle $\theta_{x1}$. At that time, the permanent magnets 12a, 12b are rotated about the rotation axis $C_x$ from the rotational positions in (a) of FIG. 13, for example, by the predetermined angle $\theta_{x1}$ in a counterclockwise direction and held at that rotational positions. Thus, the magnetic field direction B in (b) of FIG. 13 comes into a state of being tilted relative to the magnetic field direction B in (a) of FIG. 13 at the predetermined angle $\theta_{x1}$. Then, by the magnetic field direction B being changed, as shown in (b) of FIG. 13, the part at the predetermined angle $\theta_{x1}$ which is the immediately previous specific part 2a of the sample container 2 is displaced in the counterclockwise direction relative to the application position F of the X rays a, and the part at the predetermined angle $\theta_{x2}$ which is the reset specific part 2a is present at the application position F of the X rays a.

As described above, by rotating the permanent magnets 12a, 12b to change the magnetic field direction B of the time-varying magnetic field when the specific parts 2a of the sample container 2 are set, it is possible to cause any specific part 2a of the sample container 2 to come into a state of being directed in the desired direction, that is, to be present at the application position F of the X rays a, when rotation of the sample container 2 is stopped. In this state, any slit 31b of the shielding portion 31 which rotates in synchronization with the sample container 2 is located at a rotational position (the permitting position) where the X rays a are caused to pass therethrough, and thus it is possible to apply the X rays a to the sample container 2 while the rotation of the sample container 2 is stopped.

It should be noted that the other configuration of the present embodiment is the same as that of the first embodiment and thus the description thereof is omitted.

Also in the microcrystal structure analysis apparatus 1 and the microcrystal structure analysis method of the present embodiment described above, since application of the X rays a is permitted only when any specific part 2a of the sample container 2 is directed in the desired direction, it is possible to intermittently apply the X rays a to the sample in a state where any specific part 2a is directed in the desired direction. Thus, it is possible to obtain a favorable X-ray diffraction image even when the X rays a are applied to the pseudo-single-crystallized sample while the sample is rotated.

In addition, according to the microcrystal structure analysis apparatus 1 of the present embodiment, by adjusting the magnetic field direction B of the time-varying magnetic field, it is possible to direct any specific part 2a of the sample container 2 in the desired direction when the sample drive unit 13 stops rotation of the sample container 2. In this state, any slit 31b of the shielding portion 31 is located at a rotational position where the X rays a are caused to pass therethrough, and thus the X rays a are applied to the sample container 2 while the rotation of the sample container 2 is stopped. Therefore, as compared to the case where the X rays a are applied to the sample container 2 while the sample container 2 is rotated, it is possible to increase the application time per unit time, and thus it is possible to obtain a favorable X-ray diffraction image in a further short time.

Figure 14:
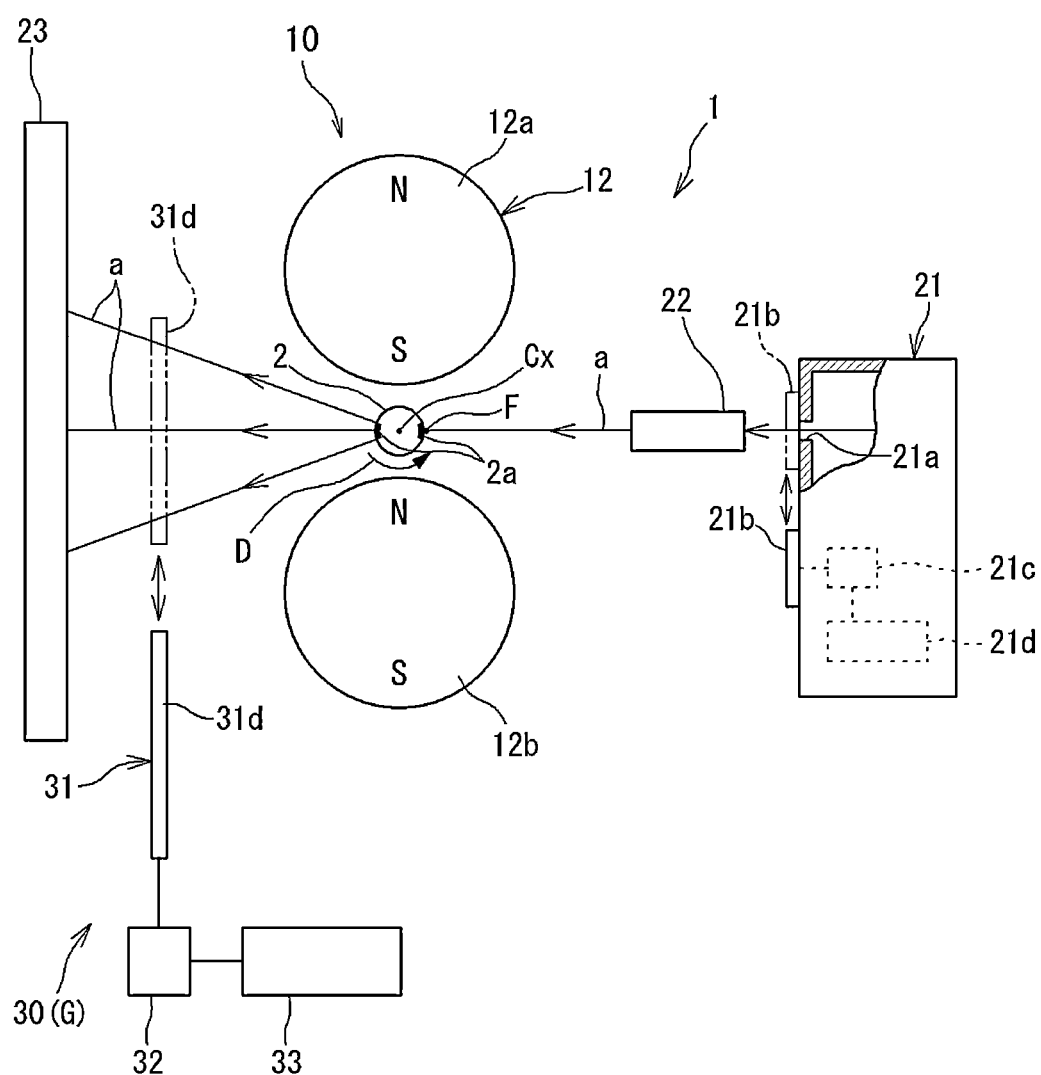
FIG. 14 is a schematic configuration diagram showing a microcrystal structure analysis apparatus according to a third embodiment of the present invention.

FIG. 14 is a schematic configuration diagram showing a microcrystal structure analysis apparatus 1 according to a third embodiment of the present invention. The microcrystal structure analysis apparatus 1 of the present embodiment is different from that of the first embodiment in that each component of the X-ray shielding device 30 is different.

As shown in FIG. 14, the shielding portion 31 of the X-ray shielding device 30 in the present embodiment is composed of a flat plate-shaped shutter 31d arranged between the sample container 2 and the X-ray detection unit 23. The shutter 31d is switchable between a shielding position (a position shown by an alternate long and two short dashes line in the drawing) and a permitting position (a position shown by a solid line in the drawing) by moving in an up-down direction which is a direction intersecting an application direction in which the X rays a are applied.

The shielding drive unit 32 of the X-ray shielding device 30 is composed of, for example, a rotary solenoid, and the shutter 31d reciprocates in the up-down direction by driving the rotary solenoid.

The shielding control unit 33 of the X-ray shielding device 30 controls driving of the shielding drive unit 32 in synchronization with rotation of the sample container 2 such that: when none of the specific parts 2a are directed in the desired direction, the shutter 31d is located at the shielding position to shield application of the X rays a; and when any specific part 2a is directed in the desired direction, the shutter 31d is located at the permitting position to permit application of the X rays a. Specifically, the shielding control unit 33 calculates a required time from a state where the rotational position of any specific part 2a coincides with the application position F to the time when the sample container 2 rotates and the rotational position coincides with the application position F next time, on the basis of the rotation speed of the sample container 2 or the like, and switches the shielding portion 31 between the permitting position and the shielding position on the basis of the required time.

In addition, the shielding control unit 33 is able to adjust the timing at which the shutter 31d is switched to each of the shielding position and the permitting position. Thus, for example, as shown in FIG. 8, when the angle $\theta_{x1}$ of each specific part 2a is reset to an angle $\theta_{x2}$ adjacent thereto, the shielding control unit 33 slightly delays the timing at which the shutter 31d is switched to each of the permitting position and the shielding position, and is able to reset each specific part 2a at the angle $\theta_{x2}$.

Furthermore, the shielding control unit 33 is able to adjust a time period for which the shutter 31d is held at the permitting position. Thus, by shortening the held time period, it is possible to decrease the angle range $\theta_{xn}$ (see FIG. 8) of each specific part 2a. In addition, reversely, by lengthening the held time period, it is possible to increase the angle range $\theta_{xn}$ of each specific part 2a.

It should be noted that the other configuration of the present embodiment is the same as that of the first embodiment and thus the description thereof is omitted.

According to the microcrystal structure analysis apparatus 1 of the present embodiment described above, since the shielding portion 31 is switchable between the shielding position and the permitting position by moving in the direction intersecting the direction in which the X rays a are applied, it is possible to obtain a favorable X-ray diffraction image with a simple configuration.

In addition, since the shielding control unit 33 is able to adjust the timing at which the shielding portion 31 is switched from the shielding position to the permitting position, it is possible to change the position of each specific part 2a of the sample container 2 to an arbitrary position along a rotation direction D in which the sample container 2 rotates. Thus, it is possible to easily reset each specific part 2a.

Furthermore, since the shielding control unit 33 is able to adjust the time period for which the shielding portion 31 is held at the permitting position, it is possible to change the size of each specific part 2a of the sample container 2 to an arbitrary size. Thus, it is possible to easily change the size of each specific part 2a in accordance with the type of the sample.

Figure 15:
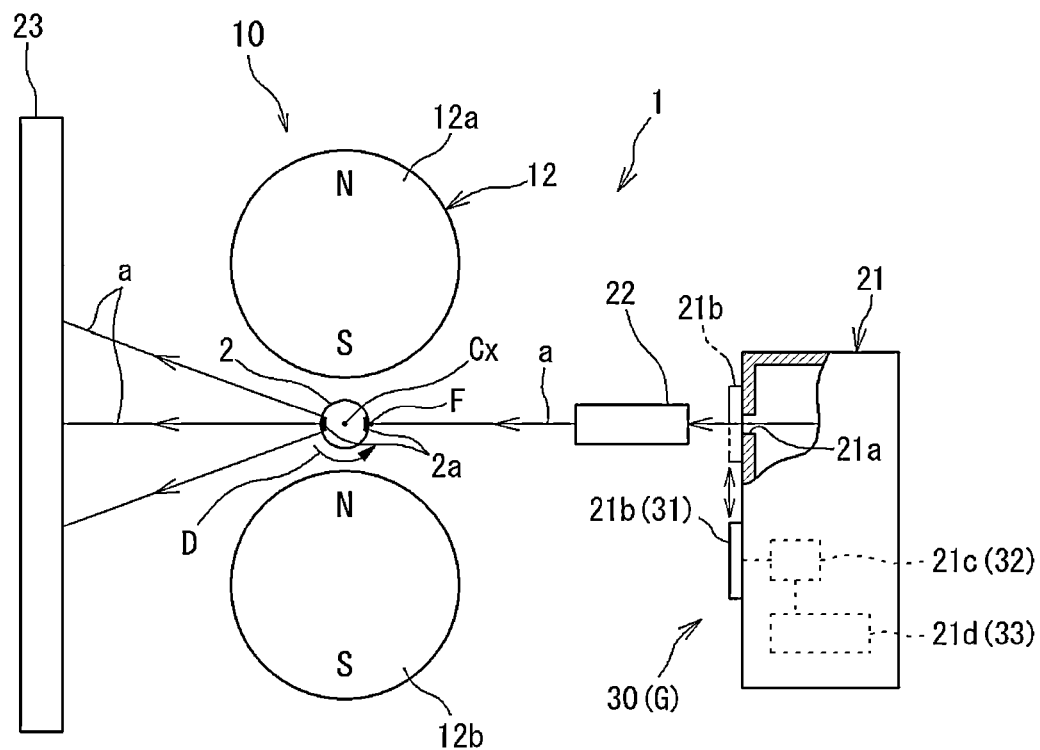
FIG. 15 is a schematic configuration diagram showing a microcrystal structure analysis apparatus according to a fourth embodiment of the present invention.

FIG. 15 is a schematic configuration diagram showing a microcrystal structure analysis apparatus 1 according to a fourth embodiment of the present invention. The microcrystal structure analysis apparatus 1 of the present embodiment is different from that of the first embodiment in that the X-ray source 21 also serves as the X-ray shielding device 30. In other words, in the X-ray shielding device 30 in the present embodiment, the shutter 21*b* of the X-ray source 21 serves as the shielding portion 31, the shutter drive unit 21*c* serves as the shielding drive unit 32, and the shutter control unit 21*d* serves as the shielding control unit 33.

The shutter control unit 21*d* controls driving of the shutter drive unit 21*c* in synchronization with rotation of the sample container 2 such that: when none of the specific parts 2*a* are directed in the desired direction, the shutter 21*b* is located at the shielding position (closing position) to shield application of the X rays a; and when any specific part 2*a* is directed in the desired direction, the shutter 31*d* is located at the permitting position (opening position) to permit application of the X rays a.

It should be noted that a specific controlling method by the shutter control unit 21*d* is the same as the driving controlling method executed by the shielding control unit 33 in the third embodiment and thus the description thereof is omitted. In addition, the other configuration of the present embodiment is the same as that of the first embodiment and thus the description thereof is omitted.

According to the microcrystal structure analysis apparatus 1 of the present embodiment described above, since the X-ray source 21 also serves as the X-ray shielding device 30, it is possible to simplify the configuration of the microcrystal structure analysis apparatus 1.

Figure 16:
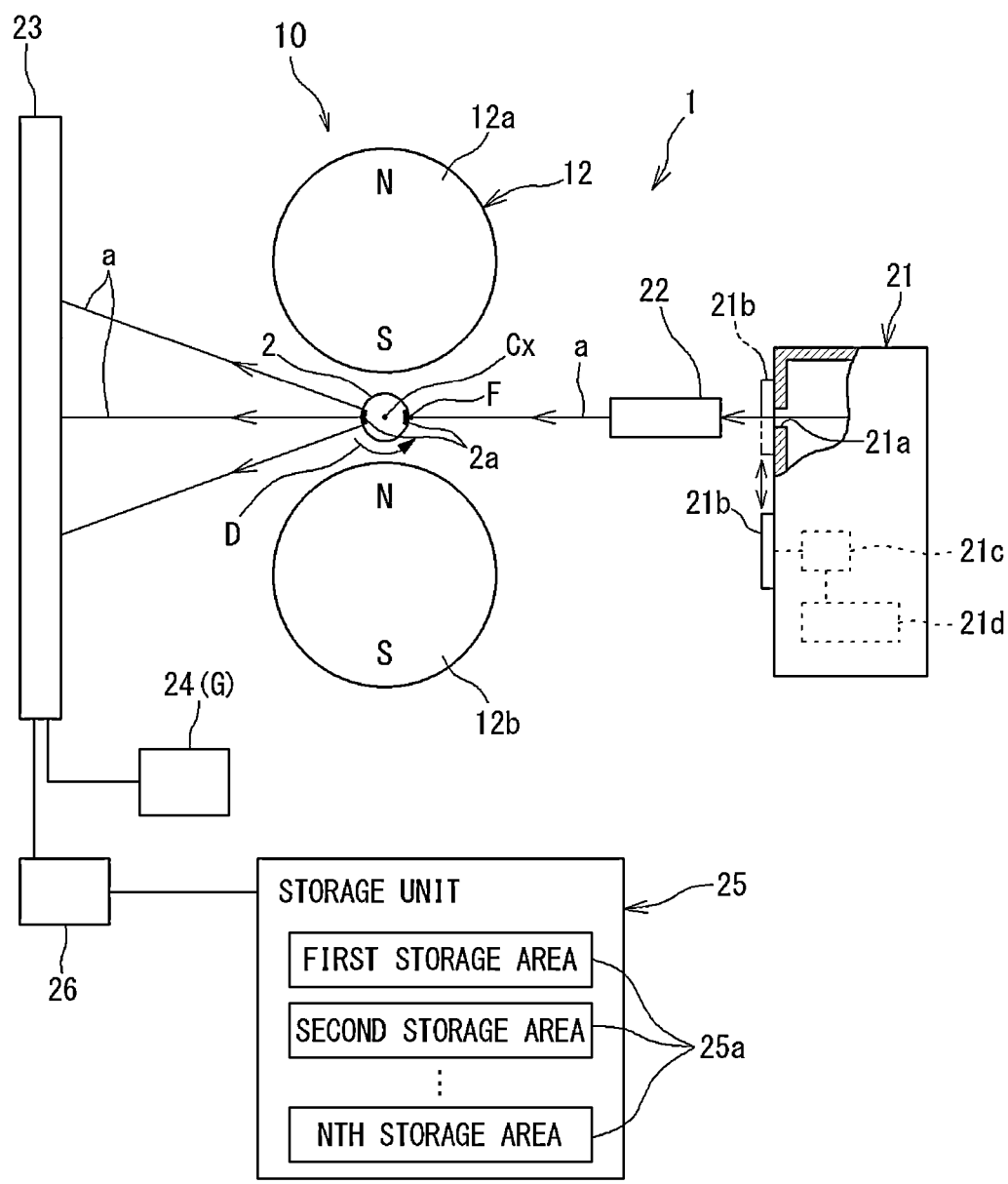
FIG. 16 is a schematic configuration diagram showing a microcrystal structure analysis apparatus according to a fifth embodiment of the present invention.

FIG. 16 is a schematic configuration diagram of a microcrystal structure analysis apparatus 1 according to a fifth embodiment of the present invention. The microcrystal structure analysis apparatus 1 of the present embodiment is different from that of the first embodiment in that it is possible to obtain a favorable X-ray diffraction image without shielding the X rays a. Specifically, the microcrystal structure analysis apparatus 1 of the present embodiment is different from that of the first embodiment in that the X-ray shielding device 30 is not provided and in that the configuration of the X-ray detection unit 23 is different.

In FIG. 16, the X-ray detection unit 23 of the present embodiment is composed of, for example, a CCD image sensor. In addition, the microcrystal structure analysis apparatus 1 of the present embodiment includes an X-ray detection control unit 24 which controls X-ray detection of the X-ray detection unit 23. The X-ray detection control unit 24 disenables X-ray detection of the X-ray detection unit 23 when any specific part 2*a* of the sample container 2 is not directed in the desired direction, and permits X-ray detection of the X-ray detection unit 23 when any specific part 2*a* of the sample container 2 is directed in the desired direction.

Therefore, the X-ray detection control unit 24 in the present embodiment is configured as a state switching device G which switches between a state where detection of the X rays a by the X-ray detection unit 23 is disenabled and a state where detection of the X rays a by the X-ray detection unit 23 is enabled, in accordance with a rotational position of each specific part 2*a*.

In addition, the microcrystal structure analysis apparatus 1 of the present embodiment is configured to perform X-ray structure analysis in a state where a plurality of (n) specific parts 2*a* are previously set along the rotation direction D in which the sample container 2 rotates. Accordingly, the microcrystal structure analysis apparatus 1 further includes a storage unit 25 which has a plurality of storage areas 25*a* which store an X-ray diffraction image obtained from the X rays a detected by the X-ray detection unit 23, for each specific part 2*a*; and a storage control unit 26 which, each time the X-ray detection unit 23 detects the X rays a through each specific part 2*a*, stores an X-ray diffraction image obtained from the X rays a into the storage area, for the corresponding specific part 2*a*, of the storage unit 25. The number of the storage areas 25*a* is set so as to coincide with the set number of the specific parts 2*a*, and the storage areas 25*a* include first to nth storage areas in the present embodiment.

The X-ray detection control unit 24 causes the X-ray detection unit 23 to detect the X rays a through each specific part 2*a* when each specific part 2*a* is sequentially directed in the desired direction while the sample container 2 makes one rotation. Then, each time an X-ray diffraction image is obtained from the X rays a through each specific part 2*a* detected by the X-ray detection unit 23, the storage control unit 26 stores the X-ray diffraction image into the storage area, for the corresponding specific part 2*a*, of the storage unit 25.

For example, in the case where the angle range $\theta_{xn}$ (see FIG. 8) of each specific part 2*a* is set to 10° and 36 specific parts 2*a* are set over the entire circumference (360°) of the sample container 2, 36 storage areas including a first storage area to a 36th storage area are set in total in the storage unit 25. When an angle range $\theta_{x1}$ of one specific part 2*a* is directed in a predetermined direction while the sample container 2 makes one rotation, the X-ray detection control unit 24 stores an X-ray diffraction image obtained from the X rays a in the angle range $\theta_{x1}$ detected by the X-ray detection unit 23, into the first storage area of the storage unit 25. At that time, if a past X-ray diffraction image is present in the first storage area, the X-ray detection control unit 24 stores the X-ray diffraction image that is to be newly stored, into the first storage area such that the X-ray diffraction image is layered on the X-ray diffraction image stored in the past.

Then, when an angle range $\theta_{x2}$ of the next specific part 2*a* is directed in the predetermined direction, the X-ray detection control unit 24 stores an X-ray diffraction image obtained from the X rays a in the angle range $\theta_{x2}$ detected by the X-ray detection unit 23, into the second storage area of the storage unit 25. At that time, if a past X-ray diffraction image is present in the second storage area, the X-ray detection control unit 24 stores the X-ray diffraction image that is to be newly stored, into the second storage area such that the X-ray diffraction image is layered on the X-ray diffraction image stored in the past.

In this manner, while the sample container 2 makes one rotation, each time an X-ray diffraction image is sequentially obtained from the X rays a in each of the angle ranges $\theta_{x1}$ to $\theta_{x36}$ of the specific parts 2*a*, the X-ray detection control unit 24 stores the X-ray diffraction image into the corresponding one of the first to 36th storage areas of the storage unit 25.

It should be noted that the other configuration of the present embodiment is the same as that of the first embodiment and thus the description thereof is omitted.

According to the microcrystal structure analysis apparatus 1 of the present embodiment described above, since the X-ray detection control unit 24 is included which controls X-ray detection of the X-ray detection unit 23 such that: when none of the specific parts 2*a* are directed in the desired direction, X-ray detection of the X-ray detection unit 23 is disenabled; and when any specific part 2*a* is directed in the desired direction, X-ray detection of the X-ray detection unit 23 is permitted, it is unnecessary to provide the shielding portion 31, the shutter 31d, or the like which shields application of the X rays a as in the first to fourth embodiments, and it is possible to simplify the configuration of the microcrystal structure analysis apparatus 1.

In addition, each time the X-ray detection unit 23 detects the X rays a through each specific part 2a, the X-ray detection control unit 24 is able to store an X-ray diffraction image obtained from the X rays a into the storage area, for the corresponding specific part 2a, of the storage unit 25. Therefore, it is possible to obtain X-ray diffraction images of the plurality of specific parts 2a while the sample container 2 makes one rotation, and thus it is possible to efficiently perform X-ray structure analysis.

It should be noted that the present invention is not limited to the above-described embodiments, and modifications may be made as appropriate to implement the present invention. For example, the shielding portion 31 in the first and second embodiments (see FIGS. 5 and 11) is arranged between the X-ray source 21 and the sample container 2, but may be arranged between the sample container 2 and the X-ray detection unit 23.

In addition, driving of the sample drive unit 13 and the shielding drive unit 32 is controlled independently by the sample control unit 14 and the shielding control unit 33, respectively, but may be controlled by a single control unit.

In addition, each slit 31b of the shielding portion 31 may be a groove having an arbitrary shape other than a recessed groove or a through hole formed so as to extend through the shielding portion main body 31a in its thickness direction.

In addition, each of the permanent magnets 12a, 12b in the above-described embodiments is formed in a spherical shape, but may be formed in another shape such as a bar shape or the like. Moreover, the magnetic field generation unit 12 in the above-described embodiments uses the permanent magnets 12a, 12b, but may use a component that generates a magnetic field, such as an electromagnet or the like.

In addition, when the X rays a are applied, the permanent magnets 12a, 12b of the magnetic field generation unit 12 in the second embodiment are held in a state where the permanent magnets 12a, 12b are adjusted by rotation, but the X rays a may be applied while being swung by the predetermined angle $\theta_{xn}$. In this case, when the X rays a are applied, it is possible to apply the X rays a to the entirety of the specific part 2a which is set at the predetermined angle $\theta_{xn}$ in the sample container 2. Thus, it is possible to obtain a further favorable X-ray diffraction image.

In addition, the magnetic field direction B of the time-varying magnetic field is adjustable by rotating the permanent magnets 12a, 12b of the magnetic field generation unit 12, but the magnetic field direction B may be adjusted by rotating the X-ray source 21, the collimator 22, the X-ray detection unit 23, and the X-ray shielding device 30 about the rotation axis $C_x$ of the sample container 2 in a state where the permanent magnets 12a, 12b of the magnetic field generation unit 12 are fixed.

In addition, the adjustment of the magnetic field direction B in the second embodiment is also applicable to the microcrystal structure analysis apparatus 1 in the third and fourth embodiments (FIGS. 14 and 15).

In addition, the shielding portion 31 in the third and fourth embodiments is switched by moving up and down, but may be switched by moving in a direction perpendicular to each of the sheet surfaces of FIGS. 14 and 15.

In addition, the shielding portion 31 in the third embodiment is arranged between the sample container 2 and the X-ray detection unit 23, but may be arranged between the X-ray source 21 and the sample container 2.

In addition, the adjustment of the timing at which the shielding portion 31 is switched and the adjustment of the time period for which the shielding portion 31 is held at the permitting position, both of which adjustments are performed by the shielding control unit 33 of the third embodiment, are also applicable to the driving control by the shutter control unit 21d (the shielding control unit 33) of the fourth embodiment.

In addition, the shutter 21b, the shutter drive unit 21c, and the shutter control unit 21d of the X-ray source 21 in the fourth embodiment also serve as the shielding portion 31, the shielding drive unit 32, and the shielding control unit 33 of the X-ray shielding device 30, but at least the shutter 21b may serve as the shielding portion 31.

In addition, the X-ray shielding device 30 in the first to fourth embodiments uses the shielding drive unit 32 and the shielding control unit 33 for switching the shielding portion 31 between the permitting position and the shielding position, but may use mechanical transmission means such as a link mechanism or the like to switch the shielding portion 31 in conjunction with rotation of the sample container 2.

In addition, the sample drive unit 13 rotates the sample container 2 relative to the magnetic field generation unit 12, but may rotate the magnetic field generation unit 12 relative to the sample container 2. In this case, the sample drive unit 13 may rotate the X-ray source 21, the collimator 22, the X-ray detection unit 23, and the X-ray shielding device 30 about the rotation axis $C_x$ of the sample container 2.

REFERENCE SIGNS LIST 1 microcrystal structure analysis apparatus
2a specific part
3 microcrystal
12 magnetic field generation unit
13 sample drive unit
21 X-ray source
21a X-ray window portion
21b shutter
23 X-ray detection unit
24 X-ray detection control unit (state switching device)
25 storage unit
25a storage area
26 storage control unit
30 X-ray shielding device
31 shielding portion
31a shielding portion main body
31b slit
32 shielding drive unit
33 shielding control unit
a X rays
B magnetic field direction
$C_x$ rotation axis
G state switching device

What is claimed is:
1. A microcrystal structure analysis apparatus comprising:
a magnetic field generation unit;
a sample drive unit configured to rotate a sample having microcrystals suspended therein relative to the magnetic field generation unit such that a temporally varying magnetic field is applied to the sample to three-dimensionally orient the microcrystals;
an X-ray source configured to apply X rays to the sample that is being rotated by the sample drive unit;

an X-ray detection unit capable of detecting the X rays that have passed through and have been diffracted by the sample; and a state switching device configured to switch between a state where detection of the X rays by the X-ray detection unit is disenabled and a state where detection of the X rays by the X-ray detection unit is enabled, in accordance with a rotational position of a specific part which is a part of the sample in a rotation direction thereof.

2. The microcrystal structure analysis apparatus according to claim 1, wherein the state switching device is composed of an X-ray shielding device configured to shield application of the X rays when the specific part is not directed in a desired direction, and permit application of the X rays when the specific part is directed in the desired direction.

3. The microcrystal structure analysis apparatus according to claim 2, wherein the X-ray shielding device includes:
a shielding portion switchable between a shielding position where the shielding portion shields application of the X rays and a permitting position where the shielding portion permits application of the X rays;
a shielding drive unit configured to switching-drive the shielding portion; and
a shielding control unit configured to control switching-driving of the shielding drive unit such that the shielding portion is located at the shielding position when the specific part is not directed in the desired direction; and the shielding portion is located at the permitting position when the specific part is directed in the desired direction.

4. The microcrystal structure analysis apparatus according to claim 3, wherein
the shielding portion includes a shielding portion main body formed in a disc shape and configured to shield application of the X rays at one surface thereof; and a slit formed in the shielding portion main body and configured to permit application of the X rays by causing the X rays to pass therethrough,
the shielding drive unit is capable of rotary-driving the shielding portion main body about an axis thereof, and
the shielding control unit controls driving of the shielding drive unit such that rotation of the shielding portion main body is synchronized with rotation of the sample.

5. The microcrystal structure analysis apparatus according to claim 4, wherein the slit is formed at two locations in a circumferential direction on the shielding portion main body with an angle difference of substantially 180 degrees therebetween.

6. The microcrystal structure analysis apparatus according to claim 4, wherein the shielding portion is arranged between the X-ray source and the sample.

7. The microcrystal structure analysis apparatus according to claim 3, wherein the shielding portion is switchable between the shielding position and the permitting position by moving in a direction intersecting an application direction in which the X rays are applied.

8. The microcrystal structure analysis apparatus according to claim 7, wherein the shielding control unit is capable of adjusting a timing at which the shielding portion is switched to each of the shielding position and the permitting position.

9. The microcrystal structure analysis apparatus according to claim 7, wherein the shielding control unit is capable of adjusting a time period for which the shielding portion is held at the permitting position.

10. The microcrystal structure analysis apparatus according to claim 7, wherein the shielding portion is arranged between the sample and the X-ray detection unit.

11. The microcrystal structure analysis apparatus according to claim 7, wherein
the X-ray source includes an X-ray window portion for emitting the generated X rays toward the sample; and a shutter configured to open and close the X-ray window portion, and
the shutter is configured as the shielding portion.

12. The microcrystal structure analysis apparatus according to claim 3, wherein
each time the sample is rotated a predetermined number of times, the sample drive unit stops the rotation for a predetermined time period, and
a magnetic field direction of the magnetic field is adjustable such that the specific part is directed in the desired direction when the sample drive unit stops the rotation of the sample.

13. The microcrystal structure analysis apparatus according to claim 1, wherein the state switching device is composed of an X-ray detection control unit configured to control X-ray detection of the X-ray detection unit such that X-ray detection of the X-ray detection unit is disenabled when the specific part is not directed in a desired direction; and X-ray detection of the X-ray detection unit is permitted when the specific part is directed in the desired direction.

14. The microcrystal structure analysis apparatus according to claim 1, wherein
a plurality of the specific parts are set along a rotation direction of the sample,
the state switching device is composed of an X-ray detection control unit configured to control X-ray detection of the X-ray detection unit such that X-ray detection of the X-ray detection unit is disenabled when none of the plurality of the specific parts are directed in a desired direction; and X-ray detection of the X-ray detection unit is permitted when any of the plurality of the specific parts is directed in the desired direction, and
the microcrystal structure analysis apparatus further comprises:
a storage unit having a plurality of storage areas configured to store an X-ray diffraction image obtained from the X rays detected by the X-ray detection unit, for each specific part; and
a storage control unit configured to, each time the X-ray detection unit detects the X rays through each specific part, store an X-ray diffraction image obtained from the X rays into the storage area, for the corresponding specific part, of the storage unit.

15. A microcrystal structure analysis method comprising:
rotating a sample having microcrystals suspended therein relative to a magnetic field generation unit, thereby applying a temporally varying magnetic field to the sample to three-dimensionally orient the microcrystals;
applying X rays toward the sample while rotating the sample;
detecting the X rays that have passed through and have been diffracted by the sample; and
switching between a state where detection of the X rays is disenabled and a state where detection of the X rays is permitted, in accordance with a rotational position of a specific part which is a part of the sample in a rotation direction thereof.

16. An X-ray shielding device provided in a microcrystal structure analysis apparatus including:

a magnetic field generation unit;

a sample drive unit configured to rotate a sample having microcrystals suspended therein relative to the magnetic field generation unit such that a temporally varying magnetic field is applied to the sample to three-dimensionally orient the microcrystals;

an X-ray source configured to apply X rays to the sample that is being rotated by the sample drive unit; and an X-ray detection unit capable of detecting the X rays that have passed through and have been diffracted by the sample, the X-ray shielding device comprising:

a shielding portion switchable between a shielding position where the shielding portion shields application of the X rays and a permitting position where the shielding portion permits application of the X rays;

a shielding drive unit configured to switching-drive the shielding portion; and a shielding control unit configured to control switching-driving of the shielding drive unit such that the shielding portion is located at the shielding position when a specific part which is a part of the sample in a rotation direction thereof is not directed in a desired direction; and the shielding portion is located at the permitting position when the specific part is directed in the desired direction, wherein:

the shielding portion includes a shielding portion main body formed in a disc shape and configured to shield application of the X rays at one surface thereof; and a slit formed in the shielding portion main body and configured to permit application of the X rays by causing the X rays to pass therethrough, the shielding drive unit is capable of rotary-driving the shielding portion main body about an axis thereof, and the shielding control unit controls driving of the shielding drive unit such that rotation of the shielding portion main body is synchronized with rotation of the sample.

* * * * *